(12) United States Patent
Zhang

(10) Patent No.: US 7,875,270 B2
(45) Date of Patent: *Jan. 25, 2011

(54) TREATMENT SOLUTION AND METHOD FOR PREVENTING POSTERIOR CAPSULAR OPACIFICATION BY SELECTIVELY INDUCING DETACHMENT AND/OR DEATH OF LENS EPITHELIAL CELLS

(75) Inventor: Jin Jun Zhang, Shanghai (CN)

(73) Assignee: Abbott Medical Optics Inc., Santa Ana, CA (US)

( * ) Notice: Subject to any disclaimer, the term of this patent is extended or adjusted under 35 U.S.C. 154(b) by 1693 days.

This patent is subject to a terminal disclaimer.

(21) Appl. No.: 11/015,532

(22) Filed: Dec. 17, 2004

(65) Prior Publication Data

US 2005/0159410 A1 Jul. 21, 2005

Related U.S. Application Data

(63) Continuation-in-part of application No. 10/244,878, filed on Sep. 17, 2002.

(51) Int. Cl.
*A61K 31/74* (2006.01)
(52) U.S. Cl. .................................. 424/78.04
(58) Field of Classification Search .............. None
See application file for complete search history.

(56) References Cited

U.S. PATENT DOCUMENTS

| 5,968,824 | A | 10/1999 | Spruce et al. |
| 6,432,934 | B1 | 8/2002 | Gilbard |

FOREIGN PATENT DOCUMENTS

| DE | 3241765 A1 | 5/1984 |
| DE | 3906311 A1 | 8/1990 |
| WO | WO9009792 | 9/1990 |

(Continued)

OTHER PUBLICATIONS

Planelli et al, Pflügers Archiv European Journal of Physiology, Springer Berlin/heildelberg, 0031-6768(Print) 1432-2013 (Online), vol. 421, No. 4/Jul. 1992, pp. 3-7-313.*

(Continued)

*Primary Examiner*—Carlos A Azpuru
(74) *Attorney, Agent, or Firm*—McAndrews, Held & Malloy, Ltd.

(57) ABSTRACT

A treatment solution used to prevent posterior capsular opacification is applied or introduced into the lens capsular bag before, during, or after cataract surgery. The treatment solution may also be applied to an intraocular lens prior to surgery. The treatment solution comprises an ion transport mechanism interference agent, which either alone or in combination with other treatment agents such as an osmotic stress agent and an agent to establish a suitable pH, selectively induces detachment and/or death of lens epithelial cells such that posterior capsular opacification is prevented. While the ion transport mechanism interference agent is capable of interfering with the cellular mechanisms and cell ion distribution of a broad range of cells, a concentration of agent is selected such that the treatment solution interferes selectively with the cellular mechanisms of lens epithelial cells while leaving other ocular cells substantially unharmed. The treatment solution selectively induces cellular death and/or detachment of lens epithelial cells while other ocular cells and tissue remain substantially unharmed and without lengthy preoperative pretreatment.

19 Claims, 17 Drawing Sheets

FOREIGN PATENT DOCUMENTS

| WO | WO9606863 A | 3/1996 |
|---|---|---|
| WO | WO0037072 | 6/2000 |
| WO | WO03026744 | 4/2003 |
| WO | WO2004026288 A | 4/2004 |
| WO | WO2004030653 | 4/2004 |

OTHER PUBLICATIONS

Use of Furosemide for the treatment of retardant formation of anterior chambers after glaucoma filtering surgery, Chinese Journal of Ocular Trauma and Occupational Eye Disease with Ophthalmic Surgery, Feb. 1999.

Cammarata P et al., "Osmoregulatory Alterations in Taurine Uptake by Cultured Human and Bovine Lens Epithelial Cells," Invest Ophthalmol Vis Sci., Feb. 2002, vol. 43, No. 2, pp. 425-433.

Clark D et al., "Inhibition of Posterior capsule opacification with an immunotoxin specific for lens epithelial cells: 24 month clinical results," J Cataract Refract Surg., Dec. 1998, vol. 24, No. 12, pp. 1614-1620.

Chung H et al., "Effect of mitomycin-C on posterior capsule opacification in rabbit eyes," J Cataract Refract Surg., Oct. 2000, vol. 26, No. 10, pp. 1537-1542.

Liu C et al., "A Study of Human Lens Cell Growth In Vitro. A Model for Posterior Capsule Opacification," Invest Ophthalmol Vis Sci., Apr. 1996, vol. 37. No. 5, pp. 906-914.

Meacock W et al., "Double-masked prospective ocular safety study of a lens epithelial cell antibody to prevent posterior capsule opacification," J Cataract Refract Surg., May 2000, vol. 26, No. 5, pp. 716-721.

McLaughlin C et al., "Timolol may inhibit aqueous humor secretion by cAMP-independent action on ciliary epithelial cells," Am J Physiol Cell Physiol, Sep. 2001, vol. 281, No. 3, pp. C865-C875.

Nishi O, "Posterior capsule opacification. Part 1: Experimental investigations," J Cataract Refract Surg., Jan. 1999, vol. 25, No. 1, pp. 106-117.

Nishi O et al., "Removal of Lens Epithelial Cells by Dispersion With Enzymatic Treatment Followed by Aspiration," Ophthalmic Surg., Aug. 1991, vol. 22, No. 8, pp. 444-450.

Parker J, "In defense of cell volume?," Am J Physiol., 1993, vol. 265, pp. C1191-C1200.

Parker J et al., "Effects of Ionic Strength on the Regulation of Na/H Exchange and K-Cl Cotransport in Dog Red Blood Cells," J Gen Physiol., Jun. 1995, vol. 105, No. 6, pp. 677-699.

Rakic J et al., "Lens Epithelial Cell Proliferation in Human Posterior Capsule Opacification Specimens," Exp Eye Res., 2000, vol. 71, No. 5, pp. 489-494.

Shin D et al., "Decrease of Capsular Opacification with Adjunctive Mitomycin C in Combined Glaucoma and Cataract Surgery," Ophthalmology, 1998, vol. 105, pp. 1222-1226.

Uebersax E et al., "Survival of the Retinal Pigment Epithelium in vitro: Comparison of Freshly Isolated and Subcultured Cells," Exp Eye Res, Mar. 2000, vol. 70, No. 3, p. 381-390.

Wagner L et al., "Effect of protein kinase Cγ on gap junction disassembly in lens epithelial cells and retinal cells in culture," Mol Vis, Mar. 2002, vol. 8, pp. 59-66.

Zhang J et al., "Volume Regulation in the Bovine Lens and Cataract. The Involvement of Chloride Channels," J Clin Invest., Feb. 1996, vol. 97, No. 4, pp. 971-978.

Zhang J et al., "The Role of Chloride in the Lens of the Eye," Exp Physiol., Mar. 1997, vol. 82, No. 2, pp. 245-259.

Zhang J et al, "A new approach to measuring transepithelial potentials in the bovine lens reveals a chloride-dependent component," Exp Physiol., Sep. 1994, vol. 79, No. 5, pp. 741-753.

Zhang J, "Three different Cl-channels in the bovine ciliary epithelium activated by hypotonic stress," J Physiol., Mar. 1997, vol. 499 (Pt. 2), pp. 379-389.

Hoffman E et al, "Membrane Mechanisms in Volume and pH Regulation in Vertebrate Cells," Physiol. Rev. Apr. 1989, vol. 69, No. 2, pp. 315-382.

Parker J, "Urea alters set point volume For K-Cl cotransport, Na-H exchange, and Ca-Na exchange in dog red blood cells," Am. J. Physiol. Aug. 1993, vol. 265 (Pt. 1), pp. C447-C452.

Sanderson J et al., "pCMPS-Induced Changes in Lens Membrane Permeability and Transparency," vol. 34, No. 8, 1993, pp. 2518-2525.

* cited by examiner

A: Anterior capsule 100, Posterior capsule 200, Capsulorhexis 300

Effect of the treatment of the combined DHCT and hyperosmotic NaCl in situ human LECs

Effect of the treatment of the combined DHCT and hyperosmotic NaCl in vivo rabbit eyes

Treated eyes

Effects of Bumetanide and hyperosmotic
NaCl on the LECs-CCC

Effects of Bumetanide and hyperosmotic NaCl on in vivo rabbits

Effects of NEM on human LECs and in vivo rabbits

Effects of Gramicidin on the LECs-CCC freshly removed from cataract surgery

TABLE 1

Table: Summary of treatment on in vivo rabbits

| Group | Eyes | Treatment | Following up (weeks) | AC reaction Cell/flare[1]; iritis[2]; posterior synechiae[3] | PCO evaluation (at 3 & 10 weeks) Gross CPCO | PPCO | Microscopy LECs |
|---|---|---|---|---|---|---|---|
| Control | 10 | PBS | 10 | +[1]; ±[2] | +++ | +++ | +++ |
|  | 4 | PBS | 3 | +[1]; ±[2] | +++ | +++ | +++ |
| DHCT | 12 | DHCT(200uM)/Hyper | 10 | +[1]; ±[2] | - | - | - |
|  | 4 | DHCT (300uM)/Hyper | 3 | +[1]; ±[2] | - | - | - |
| BUM | 5 | BUM (308uM)/Hyper | 3 | + or ++[1]; +[3] | - | - | ± |
| NEM | 2 | NEM/PBS (200uM) | 3 | ++[1] +[3] | - | - | - |
| NEM | 2 | NEM/PBS coated over the IOLs (300uM) | 3 | +[1] | - | - | - |
| NEM | 4 | NEM (200uM)/Monnitol | 10 | ++++[1]; ++[2] | - | - | - |

PBS: Phosphate Buffer Solution
Hyper: Hyperosmotic NaCl. 170 to 200mM
DHCT: Dihydrochlorothiazide 200 and 300 uM
BUM: Bumetanide 308uM
NEM: N-ethylmaleimide
GROSS: Gross evaluation by using the Miyake-Apple posterior photographic technique.
Microscopy: The lens capsules after the gross evaluation were examined under a microscopy and the presence of the cells; types of cells and cell proliferation were determined.

Anterior chamber reaction (AC reaction):

A semiquantitative grading system to be used to evaluate the inflammatory conditions of anterior chamber: aqueous flare and cells: no cell and complete absence of flare (-); 15-20 cells and very slight flare (+), 15-20 cells and moderate flare (++), 20-30 cells and marked flare (+++), >50 cells and intense flare (++++).

Evaluation of PCO
The extent and severity of PCO were scored from 1-4 according to methods reported [Nishi et al., 2001; and Pandey, Apple et al., 2002].

Figure 17

TREATMENT SOLUTION AND METHOD FOR PREVENTING POSTERIOR CAPSULAR OPACIFICATION BY SELECTIVELY INDUCING DETACHMENT AND/OR DEATH OF LENS EPITHELIAL CELLS

CROSS-REFERENCE TO RELATED APPLICATIONS

This application is a continuation-in-part of U.S. patent application Ser. No. 10/244,878 filed Sep. 17, 2002.

STATEMENT REGARDING FEDERALLY SPONSORED RESEARCH OR DEVELOPMENT

N/A

TECHNICAL FIELD

The present invention relates to novel treatment solutions and methods comprising an ion transport mechanism interference agent, alone or in combination with other agents, used to prevent posterior capsular opacification by selectively inducing detachment and/or cell death of lens epithelial cells without damaging other ocular cells and tissue and without lengthy preoperative treatment.

BACKGROUND OF THE INVENTION

The predominant role of the lens of the human eye is to focus light rays that have passed through the cornea and aqueous humour onto the retina. The structure and metabolism of the lens contributes directly toward maintaining its integrity and transparency. The lens is composed entirely of epithelial cells in different stages of maturation and is relatively unusual in that tissue is never discarded during the maturation process. As new lens cells are formed, older cells are displaced toward the interior of the lens. The lens soon becomes isolated from a direct blood supply and depends on the aqueous and vitreous humors for both nutrition and elimination pathways. The optical characteristics of the lens are much dependent on lens cells maintaining a constant cell volume and dense packing of the fibers to reduce the volume of intercellular space. Maintaining its delicate structure therefore becomes an essential characteristic of the lens. The lens has evolved its unique capabilities to maintain constant cell volume by regulating its ion, sugar, amino acid, and water balances.

A cataract of the human eye is the interruption of the transmission of light by loss of lens transparency. Cataracts, which cause blurring and clouding of vision, are by far the most common cause of low visual acuity. The clouded lens can be removed by surgical procedure, i.e. extra-capsular cataract extraction (ECCE). ECCE comprises the removal of the clinical nucleus with cortical cleanup using either manual or automated vacuuming techniques. The posterior and equatorial capsule is left intact as an envelope or bag into which a posterior chamber intraocular lens can be inserted. If the posterior capsule and zonules are intact, this lens will ordinarily remain in place throughout the patient's life without any complications. During the operation, the anterior portion of the lens capsule is carefully opened and the cataract is removed. The intraocular lens is inserted into the remaining (posterior) portion of the capsule. This also results partially in a loss of natural lens accommodation.

Standard cataract surgery employs a procedure known as phaco-emulsification. This process agitates the lens content causing break-up of the lens material, which is then sluiced out of the lens capsule by the phaco-emulsification probe that simultaneously injects and extracts a washing solution. Both dead and live lens epithelial cells detached by the treatment will be washed out by this sluicing action.

Progress is being made in the development of new treatments that involve retention of the anterior lens capsule and the replacement of the lens content with injectable material.

After this surgery, vision is restored but one of the most frequent complications of prevailing cataract surgery is the proliferation of lens epithelial cells (LECs) after cataract surgery. Posterior Capsular Opacification (PCO), also known as secondary cataract, is the most frequent complication following extra-capsular surgery, occurring in about twenty to forty percent of patients. In the past decade, results from a number of experimental and clinical studies have led to a better understanding of the pathogenesis of PCO.

The main cause of PCO is the proliferation and migration of residual LECs to the posterior lens capsule. Despite the care taken by surgeons to remove most of the residual lens epithelial cells, they are difficult to remove. Many LECs are, therefore, left behind in the lens capsular bag at the end of the surgical procedure. The proliferation of the LECs causes the membrane or envelope into which the intraocular lens is placed to become cloudy over time. Proliferation of LECs is also a significant problem in the new cataract treatments utilizing, for example, injectable lenses. The cloudy membrane is called an "after cataract" or PCO. The symptoms of PCO are identical to those of cataract, causing vision to gradually fade and eventually leading to blindness if not treated.

Much effort has been made to prevent or minimize formation of PCO. These efforts can be broadly categorized into three areas: surgical improvement, lens design improvement and chemical prevention.

A number of surgical strategies have been developed to attempt prevention of PCO. These have involved the use of various surgical instruments and the application of laser, ultrasound, and freezing techniques. Once PCO has occurred, YAG laser capsulotomy is a simple, quick procedure in which a laser beam is used to create an opening in the center of the cloudy capsule. There are, however severe risks associated with YAG laser capsulotomy. These mainly include the development of retinal detachment, glaucoma, cystoid macula oedema.

Much interest has centered on the type of material from which the intraocular lens is made and the profile of the intraocular lens' edge. Biconvex and planer convex polymethylacrylate as well as silicone plate hepatic intraocular lenses and lenses with sharp optic edges are reported to have a beneficial effect on PCO. Significant advances have been made in this area particularly by Alcon's Acrysof lens. These lenses are however relatively expensive and introduce complications or constraints of their own.

There have been other attempts to destroy or prevent proliferation of LECs making use of chemical agents. In British Patent Application 0122807.1, filed on Sep. 21, 2001, the hypothesis was that by decreasing intracellular sorbitol concentration in LECs by modulating sorbitol pathways via an aldose reductase inhibitor, PCO could be prevented by inducing death of LECs by osmotic shock. However, in order to modulate the sorbitol pathways, the proposed treatment involved pretreating the lens capsular bag for a period of up to 48 hours prior to surgery and is, therefore, not easily incorporated into current cataract surgery.

Other chemical therapies have been attempted. For example, the use of immunotoxin-conjugated antibody specific for LECs can reduce but not completely prevent the incidence of PCO. See Clark et al, J. Cataract Refract. Surg. 1998 December; 24(12): 1614-20 and Meacock et al, J. Cataract Refract. Surg. 2000 May; 26(5): 716-21. The use of ethylenediamine tetraacetic acid, Trypsin and DISPASE® (Neutral Protease) has also been used to separate the LECs but can damage the zonules and surrounding tissues. See Nishi, J. Cataract Refract. Surg. 1999 January; 25(1): 106-17 and Nishi et al, Opthalmic Surg. 1991 August; 22(8): 444-50. Other agents that have been tested for the prevention of PCO include RGD peptides to inhibit the migration and proliferation of lens epithelial cells; anti-mitotic drugs, such as Mitomycin C and 5-fluorouracil. See Chung H S, Lim S J, Kim H B. J Cataract Refract Surg. 2000 October; 26(10): 1537-42; Shin D H, Kim Y. Y., Ren J. et al. Ophthalmology. 1998; 105: 1222-1226.

Unfortunately most chemical agents described above, when used at their effective doses, demonstrate unacceptable levels of toxicity to surrounding ocular tissues including ocular cells such as corneal endothelial cells (CEDCs) and retinal pigmented epithelial cells (RPECs).

BRIEF SUMMARY OF THE INVENTION

In accordance with the present invention, the disadvantages of prior means of preventing PCO as discussed above, have been overcome. The present invention prevents PCO by rapidly and selectively inducing detachment and/or cell death of lens epithelial cells (LECs) without significantly damaging other ocular cells and tissues, is easily incorporated into existing standard cataract surgery and into future potential new treatments, and allows for easy removal of residual lens epithelial cells during or after cataract surgery. PCO prevention is accomplished via application of treatment solution or solutions. The treatment solution is applied or introduced into the lens capsular bag before, during, or after cataract surgery. Alternatively, the treatment solution may be applied to an injectable intraocular lens prior to cataract surgery. The treatment solution comprises an ion transport mechanism interference agent, which either alone or in combination with other treatment agents such as an osmotic stress agent and an agent to establish a suitable pH, selectively induces detachment and/or death of lens epithelial cells such that posterior capsular opacification is prevented. While the ion transport mechanism interference agent is capable of interfering with the cellular mechanisms and cell ion distribution of a broad range of cells, a concentration of agent is selected such that the treatment solution interferes selectively with the cellular mechanisms of lens epithelial cells while leaving other ocular cells substantially unharmed. The treatment solution selectively induces cellular death and/or detachment of lens epithelial cells while other ocular cells and tissue remain substantially unharmed and without lengthy preoperative pretreatment.

The treatment solution or solutions, which may be applied or introduced before, during, or after cataract surgery, may selectively and rapidly remove the LECs by: (i) inducing selective detachment of the LECs from their substrates or membranes through interference with normal cellular functions, causing eventual cellular death or at least allowing for easy removal of LECs; (ii) inducing selective death of LECs through interference with normal cellular functions; and/or (iii) inducing susceptibility of the LECs to osmotic stress through interference with normal cellular functions, ultimately leading to cellular detachment and/or death. The present invention allows for chemical agents that interfere with the ion transport mechanisms of a broad range of cells to specifically and uniquely target the LECs.

In one embodiment of the present invention, the ocular treatment solutions and methods prevent PCO by utilizing an ion transport mechanism interference agent to induce substantially greater incidence of detachment and/or death of LECs than other ocular cells. The ion transport mechanism interference agent of the present invention is capable of interfering, either directly or indirectly, with intracellular, extracellular and/or intercellular mechanisms that regulate the flow of ions and water across the cellular membrane of a LEC. This interference may cause cells to shrink and/or swell, resulting in cell detachment and/or death. A concentration of agent is selected such that, while the treatment solution comprising the ion transport mechanism interference agent causes significant detachment and/or death of lens epithelial cells, it does not cause the death and/or detachment of a significant percentage of other ocular cells. More particularly, the ion transport mechanism interference agent may include a co-transport interference agent, a sodium pump interference agent, an exchange interference agent, or a channel interference agent.

The ion transport mechanism interference agents may themselves induce cellular volume changes and/or cell detachment and/or death of LECs or may sensitize LECs such that the LECs are rendered incapable of sufficiently responding to an additional agent that causes osmotic stress, selectively detaching and/or killing the LEC and preventing PCO. This additional agent is an osmotic stress agent such as an osmolyte that induces osmotic shock in the LECs causing cell detachment and/or death.

The treatment solutions of the present invention have a suitable pH selected according to a selective concentration of a particular osmotic stress. The pH of the solutions can be adjusted by any acids, bases or other agent that increases or decreases the concentration of hydrogen ions in the solution.

These and other advantages and novel features of the present invention, as well as details herein, will be more fully understood from the following description.

BRIEF DESCRIPTION OF THE SEVERAL VIEWS OF THE DRAWING

FIG. 17 depicts Table 1, which is a table relating to the effects of different treatment solutions in the prevention of PCO on in vivo rabbit eyes.

DETAILED DESCRIPTION OF THE INVENTION

Figure 1:
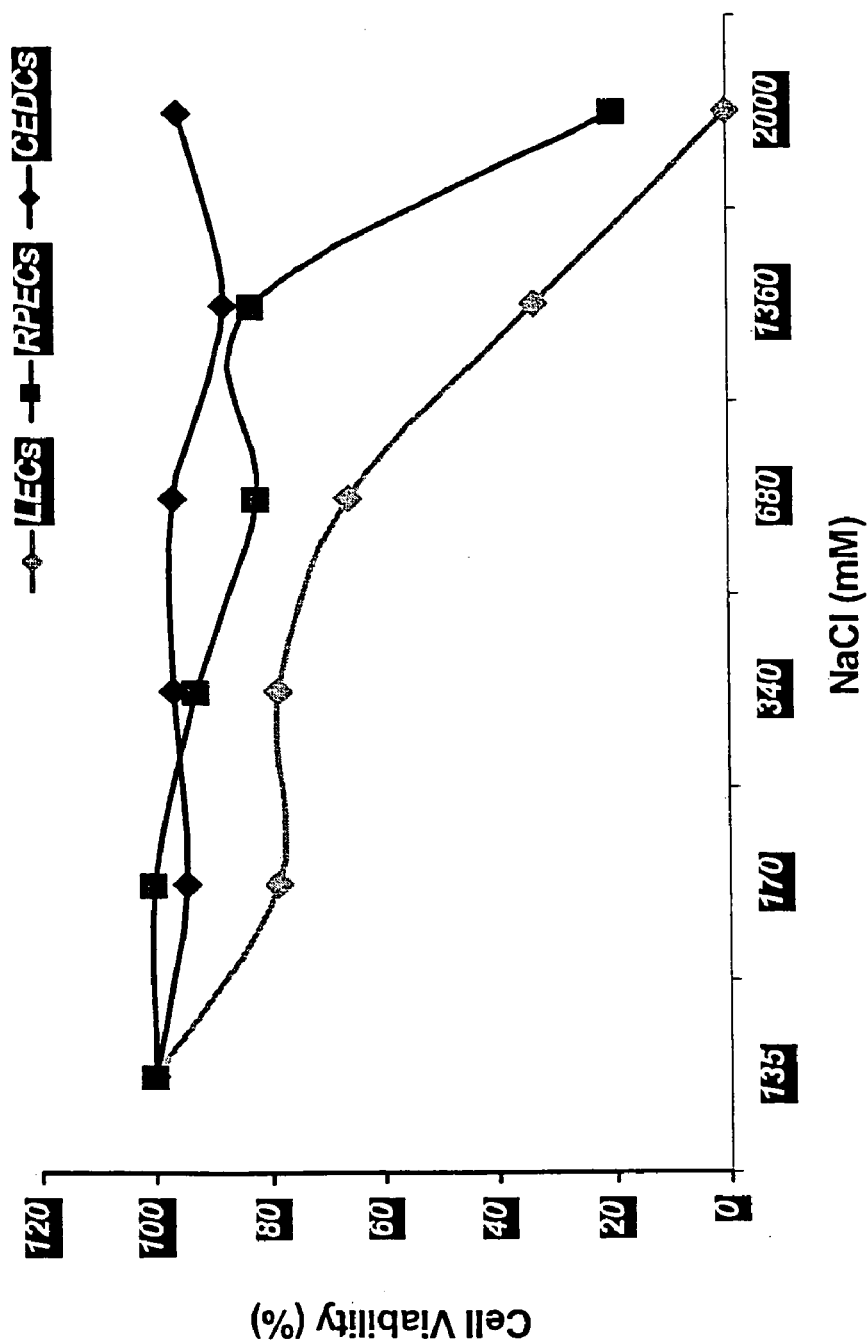
FIG. 1 is a diagram illustrating the cell viabilities of different ocular cells (LECs, RPECs and CEDCs) after solutions comprising varying concentrations of NaCl are introduced.

While the invention will be described in connection with one or more preferred embodiments, it will be understood that the invention is not limited to those embodiments. On the contrary, the invention includes all alternatives, modifications, and equivalents as may be included within the spirit and scope of the claims concluding this specification.

The present invention prevents PCO by rapidly and selectively inducing detachment from the lens capsule and/or death of lens epithelial cells via an ion transport mechanism interference agent, either alone or in combination with other agents, without substantially damaging other ocular cells and tissue and without lengthy pre-operative treatment. This selective detachment and/or death is made possible by the specific nature of LECs, which differentiates them from other cells in the eye. The result is that, at the doses and concentrations of agents used, LECs experience a change in cell volume (e.g., shrink), are detached, killed, and/or removed from the lens, whilst other ocular cells and tissue are left unharmed.

Water is effectively in thermodynamic equilibrium across the plasma membrane of human cells. Because cell membranes of virtually all human cells are highly permeable to water, cell volume is determined by the cellular content of osmotically active solutes (electrolytes and osmolytes) and by the osmolarity and/or tonicity of the extracellular fluid. Generally, intracellular and extracellular tonicity are the same; under physiological conditions, most mammalian cells are not exposed to large ranges of tonicities. The osmolarity of body fluids is normally about 285 mOsm/kg $H_2O$ and is regulated within extremely narrow limits (±3%) by body fluid homeostasis. However, under pathophysiological conditions, disturbances of body fluid homeostasis can be encountered. Plasma fluid osmolarities ranging between about 220 mOsm/kg $H_2O$ and about 350 mOsm/kg $H_2O$ have been observed. Under these extreme conditions the cells of the body would, in the absence of volume-regulating mechanisms, swell and shrink by twenty to thirty percent, respectively.

Lens epithelial cells, like other cells, use cell volume regulatory processes to defend against changes in extracellular osmolarity and to maintain constant cell volume. Volume regulatory mechanisms for lens epithelial, fibre and ciliary epithelial cells have been described earlier. See for example, C. W. McLaughlin et al, Amer. J. Phsiol. Cell Physiol. 2001 September; 281 (3): C865-75; J. J. Zhang et al, Exp. Physiol. 1997 March: 82(2): 245-59; J. J. Zhang et al, Exp. Physiol. 1994 September: 79(5): 741-53; J. J. Zhang et al, J. Physiol. 1997 Mar. 1; 499(Pt. 2): 379-89. After osmotic perturbation, there ensues a volume regulatory phase in which cells tend to return to the volume they had in an isotonic medium. Changes in cell volume activate specific metabolic and membrane transport pathways that result in the net accumulation or loss of osmotically active solutes. Regulatory volume decrease (RVD) is the process used to decrease or maintain cell volume in response to low extra-cellular osmotic pressure or tonicity. Regulatory volume increase (RVI) is the process used to increase or maintain cell volume in response to high extra-cellular osmotic pressure or tonicity. When cell solute content (i.e., intracellular tonicity) or extracellular tonicity is altered, rapid transmembrane water flow occurs to restore equilibrium. Because the plasma membrane is highly compliant, water flow causes cell swelling or shrinkage.

One way that cells alter their intracellular ion concentrations to establish equilibrium is through the use of ion transport mechanisms located on the surface of the cells. These mechanisms move ions into or out of cells, altering intracellular ion strength and, as a result, osmotic pressure. For example, the ion transport mechanisms activated during RVD in various cell types involve conductive $K^+$ and $Cl^-$ channels (separate, conductive $K^+$ and $Cl^-$ transport pathways), $K^+$—$Cl^-$ co-transport and functionally coupled $K^+$—$H^+$ and $Cl^-$—$HCO_3^-$ exchange. The ion transport mechanisms activated during RVI in various cell types involve $Na^+$—$K^+$-$2Cl^-$ co-transport, and functionally coupled $Na^+$—$H^+$ and $Cl^-$—$HCO_3^-$ exchange.

There is a surprising diversity between different cell types in the nature and reaction of ion transport mechanisms. See Hoffmann and Simonsen, Physiol Rev. 1989 April; 69 (2): 315-82. For example, there are no bumetanide-dependent ion cotransport mechanisms found in vivo corneal endothelium, but high expressions in lens epithelium. Haas, M. 1994 Am. J. Physiol. 267, C869-C885; Lawrence et al 2001, Exp. Eye Res. 73, 660. There is also a significant difference in volume set points among different cells. For example, cells have certain volume set-points at which the cells capable of undergoing RVD and RVI are doing neither. Different cells have different volume set-points at which given transport mechanisms turn on or off. See Parker, J. C Am J. Physiol. 1993, 265: C1191-1200; Parker J C et al. J Gen Physiol. 1995 June; 105(6): 677-99. The set point or threshold at which lens cells turn off their RVI and RVD processes is different from other ocular cells. Cell shape and interaction of integrins with the extra-cellular matrix play a critical role in determining cell detachment, survival or inducing programmed cell death in adherent cells. Volume regulation mechanisms are also essential for cell division. Additionally, the co-transport mechanisms may also be found in different locations in different ocular cells which may affect the outcome when a treatment is applied in the anterior chamber. For example, the cotransports in ciliary epithelium do not directly expose to the anterior chamber. (Jacob and Civann, Am. J. Physiol. 271 (40): C703-720, 1996.) These differentiate the LECs from other cells in the eye and the body.

Interfering with the ion transport mechanisms of lens epithelial cells prevents these cells from adequately responding to a hypoosmotic or hyperosmotic extra-cellular environment or other cellular stresses. The failure of the cells to respond to these stresses triggers immediate or eventual cell detachment and/or cell death.

Lens epithelial cells that are unable or rendered incapable of responding to stresses may have several responses. One response is cell death. Another possible response is detachment of the cell from its underlying substrate or membrane. For example, the cell may shrivel such that the cell can no longer maintain its attachment to the substrate, which may be associated with rearrangement of the cell cytoskeleton. Cell shrinkage may also trigger adherent cells to rearrange their focal adhesion contacts and cytoskeletal attachments to those contacts. The detachment ultimately causes cellular death and/or allows for easy removal of the cell. Cell death may lead to cell detachment from surrounding cells and the extra-cellular matrix (ECM) and cell detachment may occur without immediate cell death. For example, disruption of extra-cellular matrix contacts has been shown to induce anoikis, a form of apoptosis induced by cell detachment from its substation cells. Another possible response by lens epithelial cells is a weakening or sensitizing of the cell, such that the cell becomes vulnerable to osmotic stress or shock. For example, once a cell is sensitized, it is rendered incapable of appropriately responding to osmotic shock or stress such that introduction of shock or stressors to the sensitized cell will cause cell volume changes, detachment and/or cellular death. As shown in some examples, LEC volume changes, detachment and/or death after treatment may be evidenced by viewing the cellular area (or by other techniques including optical imaging techniques, light and epifluorescence microscopy, confocal microscopy, electron microscopy, immunofluorescence techniques, in situ hybridization techniques and techniques for protein identification and analysis) before or after the area has been rinsed, washed, or in any way agitated such that detached and/or dead LECs may be removed. The treatment solutions and methods of the present invention prevent PCO by selectively and rapidly eliciting at least one of these responses from LECs while leaving other ocular cells substantially unharmed.

In one aspect, the ocular treatment solutions and methods of the present invention prevent PCO by inducing substantially greater incidence of detachment of the LECs from their substrates or membranes and/or cell death than other ocular cells such as corneal endothelial cells (CEDCs) and retinal pigmented epithelial cells (RPECs) via an ion transport mechanism interference agent. Therefore, a significant advantage of the present invention is that treatment with the agents of the present invention prevents PCO by allowing for removal from the lens capsular bag of a substantial percentage of LECs, while other ocular cells and tissue are not significantly harmed.

The ion transport mechanism interference agent is an agent capable of interfering, either directly or indirectly, with intracellular, extracellular and/or intercellular mechanisms that regulate the flow of ions and water across or within the cellular membrane of a lens epithelial cell. The ion transport mechanism interference agent interferes with normal cellular ion distribution mechanisms and consequently the functions of cells. The ion transport mechanism interference agent of the present invention, either alone or in combination with other agents, disturbs the normal distribution of LEC cell ions and thereby selectively induces, either directly or indirectly, LEC detachment and/or death to prevent PCO. A concentration of the agent is selected such that the treatment solution interferes with ion transport mechanisms of LECs causing cellular volume changes, detachment and/or death of LECs, but does not substantially interfere with ion transport mechanisms of other ocular cells. While LECs may be easily removed from the lens capsular bag due to cell detachment and/or death, other ocular cells remain substantially unharmed.

The ion transport mechanism interference agent is capable of interfering with one or more of the following cellular mechanisms in an LEC: (1) co-transport mechanisms (for example, $K^+$—$Cl^-$ co-transport, $Na^+$—$Cl^-$ co-transport, $Na^+$—$K^+$-$2Cl^-$ co-transport and amino acid transport); (2) the sodium pump; (3) ion exchanges (for example, functionally coupled $Na^+$—$H^+$ and $Cl^-$—$HCO_3^-$ exchanges; functionally coupled $K^+$—$H^+$ and $Cl^-$—$HCO_3^-$ exchange, $Cl^-$—$Cl^-$ exchange, $Ca^{2+}$—$Na^+$ exchange); and (4) ion channels (for example, potassium channels, chloride channels, volume-sensitive organic osmolyte and anion channel (VSOAC), pore-forming proteins and peptides and other anion channels). The ion transport mechanism interference agent may activate or inhibit either directly or indirectly these cellular mechanisms.

In hypotonic media, vertebrate cells initially swell by osmotic water equilibration but subsequently regulate their volume by a net loss of KCl and a concomitant loss of cell water to restore normal cell volume. Cell swelling activates transport pathways that result in the net efflux of potassium, chloride and organic osmolytes. The ion transport mechanisms activated during RVD in various cell types involve conductive $K^+$ and $Cl^-$ channels (separate, conductive $K^+$ and $Cl^-$ transport pathways), $K^+$—$Cl^-$ co-transport, and functionally coupled $K^+$—$H^+$ and $Cl^-$—$HCO_3^-$ exchange. For example, potassium and chloride are lost from the cell primarily through activation of the $K^+$—$Cl^-$ co-transport or through separate potassium and anion channels.

In contrast, in hypertonic media, vertebrate cells initially shrink by osmotic water equilibration but subsequently regulate their volume by a net gain of KCl and a concomitant uptake of cell water to restore normal cell volume. Cell shrinkage activates transport pathways that result in the net influx of chloride, sodium, and potassium. The ion transport mechanisms activated during RVI in various cell types involve $Na^+$—$Cl^-$ or $Na^+$—$K^+$-$2Cl^-$ co-transport, and functionally coupled $Na^+$—$H^+$ and $Cl^-$—$HCO_3$ exchange.

Examples of ion transport mechanism interference agents include, but are not limited to:
n-ethylmaleimide
valinomycin
gramicidin
catecholamines
calcium Ionophore A23187 (including, for example, Ionophore A23187 plus calcium)
  calmodulin
  pimozide
  loop diuretics (e.g., frusemide, bumetanide, ethacrynic acid, piretanide, torasemide)
  thiazide diuretics (e.g., dihydrochlorothiazide; hydrochlorothiazide; cyclopenthiazide; benzthiazide; chlorothiazide; bendroflumethiazide; chlorthalidone; hydroflumethiazide; methyclothiazide; metolazone; polythiazide; quinethazone; trichlormethiazide)
  amiloride
  di-isothiocyano-disulfonyl stilbene (DIDS)
  staurosporine (SITS)
  niflumic acid
  stilbene derivatives (e.g. 4,4'-dinitrostilbene-2'2-disulfonic acid)
  quinine
  Cytochalasin B In general there are four classes of ion transport mechanism interference agents: (1) co-transport interference agents; (2) sodium pump interference agents; (3) exchange interference agents; and (4) channel interference agents. As reflected below, it is understood that an ion transport mechanism interference agent may fall into one or more of the four preceding classes.

A co-transport interference agent is an agent capable of interfering, either directly or indirectly, with the co-transport mechanisms of a cell. More particularly, the co-transport interference agent activates or inhibits the co-transport mechanisms of an LEC. A concentration of co-transport interference agent is selected such that the treatment solution induces substantially greater incidence of detachment and/or death of LECs than other ocular cells. Examples of co-transport mechanisms include the $K^+$—$Cl^-$ or $Na^+$—$K^+$-$2Cl^-$ cotransports. Examples of co-transport interference agents include:

Diuretics, for example:

(i) thiazide diuretics such as Dihydrochlorothiazide, Hydrochlorothiazide, Cyclopenthiazide, Benzthiazide, Chlorothiazide, Bendroflumethiazide, Chlorthalidone, Hydrochlorothiazide, Hydroflumethiazide, Methyclothiazide, Metolazone, Polythiazide, Quinethazone, and Trichlormethiazide. Commonly used brand names in the United States include: Aquatensen (methyclothiazide), Diucardin (hydroflumethiazide), Diulo (metolazone), Diuril (chlorothiazide), Enduron (methyclothiazide), Esidrix (hydrochlorothiazide), Hydro-chlor (hydrochlorothiazide), Hydro-D (hydrochlorothiazide), HydroDIURIL (hydrochlorothiazide), Hydromox (quinethazone), Hygroton (chlorthalidone), Metahydrin (trichlormethiazide), Microzide (hydrochlorothiazide), Mykrox (metolazone), Naqua (trichlormethiazide), Naturetin (bendroflumethiazide), Oretic (hydrochlorothiazide), Renese (polythiazide), Saluron (hydroflumethiazide), Thalitone (chlorthalidone), Trichlorex, (trichlormethiazide), Zaroxolyn (metolazone), Apo-Chlorthalidone (chlorthalidone), Apo-Hydro (hydrochlorothiazide), Diuchlor H (hydrochlorothiazide), Duretic (methyclothiazide), HydroDIURIL (hydrochlorothiazide), Hygroton (chlorthalidone), Naturetin (bendroflumethiazide), Neo-Codema (hydrochlorothiazide), Novo-Hydrazide (hydrochlorothiazide), Novo-Thalidone (chlorthalidone), Uridon (chlorthalidone), Urozide (hydrochlorothiazide), and Zaroxolyn (metolazone)

(ii) loop-acting diuretics such as benzmetanide, bumetanide, torsemide, ethacrynic acid, and frusemide (also known as furosemide). Commonly used brand names include: Bumex (bumetanide), Demadex (torsemide), Edecrin (ethacrynic acid), Lasix (furosemide), Myrosemide (furosemide), Apo-Furosemide (furosemide), Edecrin (ethacrynic acid), Furoside (furosemide), Lasix (furosemide), Lasix Special (furosemide), Novosemide (furosemide), and Uritol (furosemide)

(iii) potassium-sparing diuretics. Communly used brand names in the United States include as Aldactone (spironolactone), Dyrenium (triamterene), and Midamor (amiloride). Commonly used brand names in Canada: Aldactone (spironolactone), Dyrenium (triamterene), Midamor (amiloride), and Novospiroton (spironolactone))

(iv) carbonic anhydrase inhibitors such as Acetazolamide, Dorzolamide and Brinzolamide (v) diuretics with potassium such as Burinex K® (Leo), Centyl K®; Lasikal®, and Neo-NaClex-K®

(vi) combined diuretics such as Triam-co [co-triamterzide 50/25]; Amil-co [co-amilozide 5/50], co-amilozide 5/50 [co-amilofruse 5/50], Moduretic [co-amilozide 5/50], Dyazide [co-triamterzide 50/25], Navispare [amiloride 2.5 mg+cyclopenthiazide 250 mcg], co-amilofruse 5/40 [co-amilofruse 5/40] Fru-co [co-amilofruse 5/40] Frusene [triamterene 50 mg+frusemide 40 mg], Kalspare [triamterene 50 mg+chlortalidone 50 mg]; Burinex A [amiloride 5 mg+bumetanide 1 mg] Lasoride [co-amilofruse 5/40], Frumil [co-amilofruse 5/40] Lasilactone [spironolactone 50 mg+frusemide 20 mg], Aldactide 50 [co-flumactone 50/50], and Dytide [triamterene 50 mg+benzthiazide 25 mg]; Co-flumactone [Spironolactone with thiazides]).

Examples of co-transport interference agents also include:

co-transport interference agents that cause cell shrinkage by promoting increase of KCl efflux via K—Cl co-transport include DDS-NOH, Dihydroindenyl[oxy]alkanoic acid (DIOA), okadaic acid (OA), A-23187, 1-ethyl-2-benzimidazolinone, YM934, cromakalim, gem-dimethyl substituent: 9-(3,4-dichlorophenyl)-3,4,6,7,9,10-hexahydro-1,8(2H, 5H)-acridinedione (A-184208), charybdotoxin (ChTX), Prostaglandin E2, staurosporine, K+ ionophore valinomycin, tumor necrosis factor α plus cycloheximide, diazoxide, pinacidil and nicorandil, and agents that increase intracellular levels of cAMP or cyclic GMP (Nelson et al., 1995), and epoxides of arachidonic acid.

any stimuli that induces potassium and chloride and other ion and osmolyte loss (for example, intracellular or extracellular calcium depletion or elevation) by activation of K—Cl co-transport mechanisms n-ethylmaleimide (NEM) (including, for example, n-ethylmaleimide plus rubidium)
  iodoacetamide
  mercury ($Hg^{2+}$)

and any other agent capable of capable of activating or inhibiting a co-transport mechanism of a lens epithelial cell.

A sodium pump interference agent is an agent capable of interfering, either directly or indirectly, with the Na/K/ATPase pump, known as the sodium pump, mechanism of a cell. More particularly, the sodium pump interference agent activates or inhibits the Na/K/ATPase pump of an LEC. For example, LECs contain impermanent, anionic macromolecules and the colloid-osmotic swelling, resulting from entry of diffusible ions and water (Gibbis-Donnan equilibrium), is constantly counteracted by the operation of ion-extruding pumps that extrude ions at a rate equal to that of the dissipative leak entry. A concentration of a sodium pump interference agent is selected such that the treatment solution induces substantially greater incidence of detachment and/or death (e.g., via swell) of LECs than other ocular cells. An example of a sodium pump interference agent includes ouabain and any other agent capable of activating or inhibiting a sodium pump of a lens epithelial cell.

Yet another type of ion exchange mechanism interference agent is an exchange interference agent. An exchange interference agent is an agent capable of interfering, either directly or indirectly, with the ion exchanges of a cell. More particularly, the exchange interference agent activates or inhibits the ion exchange mechanisms of a LEC, which not only results in intracellular and extracellular ion re-distribution but may also alter intracellular pH. Examples of ion exchange mechanisms include $K^+$—$H^+$ and $Cl^-$—$HCO_3$ exchanges and $Na^+$—$H^+$ exchange functionally coupled to $Cl^-$—$HCO_3$ exchange. For example, any stimuli that induce potassium and chloride loss by activation of the $K^+$—$H^+$ and $Cl^-$—$HCO_3^-$ exchanges of an LEC is an exchange interference agent. Examples of exchange interference agents include:

staurosporine (SITS)
amiloride
di-isothiocyano-disulfonyl stilbene (DIDs)
calmodulin (CaM)
copper ($Cu^{2+}$)
hydrogen ($H^+$)
and any other agent capable of activating or inhibiting an exchange of a lens epithelial cell.

A channel interference agent is an agent capable of interfering, either directly or indirectly, with the ion channels of a cell. More particularly, the channel interference agent activates or inhibits the ion channels of an LEC. Examples of ion channel include the potassium, chloride, sodium, and VSOAC and pore-forming proteins and peptides channels or transport pathways. For example, any stimulus that induces potassium chloride and organic osmolyte loss by activation of potassium and chloride channels is a channel interference agent. A concentration of a channel interference agent is selected such that the treatment solution induces substantially greater incidence of detachment and/or death of LECs than other ocular cells. Examples of channel interference agents include:

ketoconazole (KETO)
5-nitro-2-(3-phenylpropylamino)benzoic acid (NPPB)
1,9,-dideoxyforskolin (DDF)
tamoxifen
verapamit
quinine
barium ($Ba^{2+}$)
diphenylamine-2-carboxylate (DPC)
anthracene-9-carboxylic acid
indocrinone (M–196)
pimozide
CBIQ
EBIO, 1-ethyl-2-benzimidazolone
tamoxifen+ATP
Sulfhydryl oxidizing agents
inhibitors of protein phosphorylation
4-chloro-benzo[F]isoquinoline
β-CCM, ZK 93426
flumazenil
adenosine
sulfonylurea
arachidonic acid (AA)
phospholipase C (PLC)
protein kinase C
G-proteins
agents that induce changes in F-actin organization
and any other agent capable of activating or inhibiting an ion channel of a lens epithelial cell.

Pore-forming proteins and peptides are the agents capable of creating a pathway of a lens epithelial cell for molecules that cannot normally cross their lipid bilayer. More particularly, these PPFPs form a pore or channel to promote intracellular K leak out from an LEC. Hundreds of peptide antibiotics have been described in the past half-century including gramicidin, bacitracin; polymyxin (B) (Neosporin, Otosporin), Nystatin (Nystan, Tri-Adcortyl), glycopeptides, a-defensin, b-defensin 1, tachyplesin, bacterial nisin, a-hemolysin, roimmunolysins, Porins (OmpA, PhoE, NmpC, OmpF, Phosphoporin, LamB porin), Bcl-XL; α-hemolysin; Aerolysin, colicins, alamethecin, magainin, cecropin; amphiphilic β sheet peptides (gramicidin, defensin, and cytolysin), α-helical peptides (alamethecin, pneumolysin, magainin and cecropin), ranalexin, brevinin, and PR39.

Using the agents of the present invention, a concentration of agent or agents is selected such that application of the treatment solution results in LEC cell viability of preferably less than about ten percent, more preferably less than about five percent, and more preferably approaching zero percent. The desired cell viability for other ocular cells such as RPECs and CEDCs is preferably greater than about seventy percent, more preferably about ninety percent, and more preferably approaching one hundred percent.

Under these circumstances, the treatment solution comprising the agent, perhaps in combination with other agents, selectively induces LECs detachment and/or death and induces substantially greater incidence of detachment and/or death of LECs than other ocular cells. As shown in the examples, cellular detachment and/or death may be evidenced by viewing the cellular area before or after the area has been rinsed, washed, or in any way agitated such that detached and/or dead LECs may be removed.

The agents of the present invention described above (referred to hereafter as the primary agent) selectively induce detachment and/or death of an LEC, directly or indirectly, alone or in combination with additional agents described below or other agents and/or chemicals. For example, the ocular treatment solutions and methods of the present invention may comprise an osmotic stress agent, in addition to the primary agent, wherein the solution induces substantially greater incidence of cell detachment and/or death of lens epithelial cells than corneal endothelial cells and retinal pigmented epithelial cells to prevent posterior capsular opacification.

An osmotic stress agent is an agent capable of inducing osmotic shock in an LEC. Osmotic shock in an LEC may be caused by any cellular condition that alters normal intracellular or extracellular ion equilibrium. For example, changes in the extracellular concentrations of osmotically active solutes and various stimuli that affect the activity of the specific ion transport systems involved in cell volume control (e.g., hormones, growth factors and other external stimuli, the cell membrane potential, and cytoplasmic second messengers) may induce osmotic shock. Large transcellular ion fluxes may shock cellular volume homeostasis. Hypoosmotic stress can be caused by exposure of cells to a hypotonic solution or a solution with a hypoosmotic osmolarity. Conversely, hyperosmotic stresses can be caused by exposure of cells to a hypertonic solution or a solution with a hyperosmotic osmolarity. An increase or decrease in the cellular concentration of osmotically active ions and organic solutes may also shock cellular volume regulation and activate membrane transport processes involved in the RVD or RVI response.

The application or introduction of an osmotic stress agent is appropriate where the primary agent sensitizes the LEC to osmotic shock (for example, by inhibiting an ion transport mechanism) and where the osmotic stress agent itself induces cell detachment and/or death. For example, if the ion transport mechanism interference agent inhibits an essential ion transport mechanism such as the sodium-potassium pump or co-transport, the LEC is incapable of defending itself against external osmotic stresses or shocks, thereby enhancing its sensitivity to extracellular osmotic pressure caused by an additional osmotic stress agent. The failure of LECs to respond to osmotic stresses or shocks may trigger cell death through activation of death-signaling processes.

However, it is understood that the primary agents may also be osmotic stress agents such that a primary agent may both selectively interfere with the ion transport mechanisms of LECs and induce osmotic shock.

More particularly, the osmotic stress agent has a hyperosmotic or hypoosmotic osmolarity. A hypoosmotic solution is one that has a lower solute concentration than that normally found in physiological conditions; a hyperosmotic solution has a higher solute concentration than that normally found in physiological conditions. In other words, the osmotic stress agent creates extracellular hypertonicity or hypotonicity.

Any physiologically tolerable electrolytes and osmolytes, any solute that contributes to osmotic strength, are suitable for inducing osmotic stresses or shocks. Examples of osmolytes include:

salts (such as NaCl) including:

(i) inorganic salts with cations including sodium, potassium, lithium, rubidium, beryllium, magnesium, calcium, strontium, barium, aluminum, zinc, tin, silver, gold, iron, mercury and corresponding anions including chloride, bromide, iodide, hydroxide, borate, metaborate, carbonate, hydrogen carbonate, nitrate, fluoride, sulfate, monophosphate, diphosphate, phosphate, thiocyanate and isothocyanate (ii) organic salts with the same cationic ions as above and corresponding anions such as acetate, alginate, benzoate, butyrate, caprylate, caproate, citrate, decansulfonate, decylsulfate, dodecylsulfate, diethyl barbiturate, dimethyldithiocarbamate, dithionite, dodecansulfonate, ethansulfonate, fluoroacetate, fluorophosphates, furmarate, hexafluorophosphate, hexansulfonate, iodoacetate, L-lactat, D-lactat, D,L-lactat, maleinate, malonate, mesolaxate, myristate, oleate, oxalate, palmitate, propionate, salicylate, tartrate, and trifluoro acetate;

amino acids (such as taurine, glycine, and alanine);

sugars (such as mannitol, myo-inositol, betaine, glycerophosphorylcholine, betains, urea, sucrose and glucose);

and any other organic or inorganic osmolytes.

It is noted that while the osmolyte may be sodium chloride, as described above, the chloride may be replaced by iodide, bromide, nitrate, thiocyanate, fluoride, sulfate, isethionate, gluconate, and any other acceptable substitute; similarly, sodium may be replaced by potassium, cesium, rubidium, lithium, francium, and any other acceptable substitute.

Preferred osmolytes are sodium chloride, potassium chloride, sodium bromide, sodium citrate, sodium lactate, sodium hydroxide, sodium iodide, sodium carbonate, sodium hydrogen carbonate, sodium nitrate, sodium fluoride, sodium sulfate, potassium carbonate, potassium citrate, potassium lactate, potassium hydrogen carbonate, potassium bromide, potassium hydroxide, potassium iodide, potassium nitrate, potassium sulfate, cesium chloride, rubidium chloride and lithium chloride.

The osmotic stress agent and the primary agent may be applied separately, simultaneously or sequentially in the treatment of PCO.

The treatment solution may preferably have a pH from about 5 to 11, depending on the agents and concentrations used. In a preferred embodiment, a treatment solution comprising approximately ±200 mM NaCl, and more preferably ≦200 mM NaCl, has a pH preferably in the range of about 8 to 10, more preferably 7 to 10, and more preferably 7.6. The pH of the treatment solution may be adjusted by varying the concentrations of the primary agents or the osmotic stress agent or by the introduction of an additional chemical agent that alters the pH. The pH can be adjusted by any acids or bases or any agent that increases or reduces the hydrogen ion concentration.

The treatment will work with a range of concentrations of primary agents, osmotic stress agents and agents which adjust pH. In accordance with the present invention, suitable concentrations of agents are selected such that an agent that may be capable of interfering with the cellular mechanisms of a broad range of cells selectively interferes with the ion transport mechanisms of LECs, causing LEC detachment and/or death. Application of the treatment solution results in a significant percentage of LECs that are detached and/or killed whilst a low percentage of other ocular cells are harmed. At one end of the range of concentrations, the efficiency of the treatment solution is reduced, resulting in longer times to kill the LEC cells. At the other end of the range the medicament is prone to damaging other cells in the eye. Suitable concentrations of both the primary agent, the osmotic stress agent and the agents which adjust pH should be selected such that PCO may be prevented by selective cell death and/or detachment of LECs without significant damage to other ocular cells and ocular tissue. Preferably, concentrations of the agent or agents should be selected such that, upon application, cell viability for LECs is less than about ten percent, more preferably less than about five percent, and more preferably approaching zero percent and the cell viability for other ocular cells such as RPECs and CEDCs is greater than about seventy percent, more preferably greater than about ninety percent, and more preferably approaching one hundred percent. The concentration of active ingredients depends on the pharmacological activity of the active ingredients, but is generally preferably less than 1500 µM, more preferably lower than 1000 µM, and more preferably lower than 500 µM.

The agents described above and the concentrations in which they are introduced are interrelated. For example, a high pH treatment solution will kill LECs with lower levels of osmolarity. Examples of suitable concentrations of certain agents are provided in the examples below. Moreover, the concentrations can be adjusted to suit the particular needs of prevailing cataract surgery techniques and the needs of the patient.

The treatment solution of the present invention may be administered before, during, or after cataract surgery to prevent PCO. The anterior portion of the lens capsule is opened and the cataract removed. The intraocular lens may then be inserted into the posterior portion of the capsule. Alternatively, the lens or lens content may be replaced with an injectable intraocular lens (also known as lens refilling technique). The intraocular lens and lens materials may be pretreated with the treatment solution of the present invention before it is placed into the lens capsule bag (e.g., by injection or insertion). The residual LECs may or may not be removed using vacuuming or other surgical techniques. Phaco-emulsification, laser or other techniques may be employed to remove the lens contents. The treatment solution or treatment solutions may be applied or introduced topically at any time before, during or after this process. The ocular region may then be washed to remove residual cells.

As described above, the treatment solution may comprise the primary agent, the osmotic stress agent, and any chemical agent used to adjust the pH of the solution. Alternatively, separate solutions comprising the primary agent, the osmotic stress agent, and/or the chemical agent to adjust pH may be applied or introduced either sequentially or simultaneously to prevent PCO. As described above, the primary agent may also be an osmotic stress agent. The solution or solutions may be applied via syringe, dropper, probe used for phaco-emulsification or any other suitable or convenient means of application.

An additional advantage of the present invention is that the treatment solutions induce relatively rapid cell volume changes (e.g., shrinkage, detachment and/or death of lens epithelial cells such that the treatment of the present invention is easily incorporated into cataract surgery. Detachment of lens epithelial cells may occur within about thirty minutes of application of the solution or agents of the present invention, with cell death occurring within several hours. Preferably, cell volume changes and/or detachment occur within about fifteen minutes of application but is dependent on the concentrations and agents selected.

Whether the treatment solutions and methods of the present invention have induced substantially greater incidence of cell detachment and/or death of LECs than other ocular cells or whether such treatment is selective may be determined by a comparative assessment of cell viability after treatment or any other acceptable method of determining effectiveness. More particularly, the treatment solutions and methods should prevent PCO while causing only minimal physiological damage to other ocular cells as described. Preferably, concentrations of the agent or agents should be selected such that, upon application, cell viability for LECs is less than about ten percent and the cell viability for other ocular cells such as RPECs and CEDCs is greater than about seventy percent. It is understood that the treatment solution or solutions may comprise additional agents, chemicals, proteins, and/or substances and may comprise more than one primary agent or osmotic stress agent. Additional chemical or biological components may be added to improve the properties of the treatment solution or solutions, for example, physiological tolerance, viscosity or storage capability.

The treatment solution may be used to coat an intraocular lens and/or intraocular lens materials prior to cataract surgery or may be mixed with intraocular lens materials for use when a lens refilling technique is employed. The treatment solution may be packaged in kits or other packaging or stored either as a unitary solution or, as described above, in separate solutions for later application. For example, a kit or package may include a solution containing the ion transport mechanism interference agent packaged separately from a solution containing the osmotic stress agent. Furthermore, the treatment solution may be packaged in kits or packaging containing fluids used during phaco-emulsification or in kits used for removal of lens content prior to injection of an injectable intraocular lens.

EXAMPLES

Comparative Example 1

As described below, the confluent monolayers of LECs, CEDCs, and RPECs grown in 96-well flat-bottom plates are exposed to varying concentrations of NaCl (an osmolyte) solution. Two hundred µl of NaCl solution (prepared as described below) are added to each well at concentrations of 137 mM, 170 mM, 340 mM, 680 mM, 1360 mM and 2000 mM NaCl, respectively. The solutions have a pH of 8.0±0.4. The concentrations of NaCl correspond to final osmolarities of about 285 to 4000 mOsm/L, respectively. Within about five to ten minutes after addition of hypertonic NaCl, some of the LECs began to shrink, round up and lose adhesion from the monolayer in a dose-dependent manner. This effect is not seen as significantly in the CEDCs and RPECs.

Cell viabilities of LECs, CEDCs and RPECs in response to increasing hyperosmotic NaCl are shown in FIG. 1 (LECs shown in light gray diamonds, RPECS in dark gray squares, CEDCs in black diamonds). Each point represents the mean of two experiments. At a hypertonic stress of about 1380 mM NaCl, about forty percent of the LECs survive while more than eighty percent of CEDCs and RPECs survive, evidencing the different osmotic tolerance between these cells.

The primary and first passages of human lens epithelial cells, human corneal endothelial cells, and human retinal-pigmented epithelial cells are cultured. The LECs, the CEDCs, and the RPECs are isolated from post-mortem eyes by using standard techniques of cell isolation and enzyme digestion. See Uebersax E D, Grindstaff R D and Defoe D M Exp Eye Res. 2000 March; 70(3): 381-90; Wagner L M, Saleh S M, Boyle D J, and Takemoto D J. Mol Vis. 2002 Mar. 14; 8: 59-66; Cammarata P R, Schafer G, Chen S W, Guo Z, and Reeves R E. Invest Ophthalmol Vis Sci. 2002 February; 43(2): 425-33; Rakic J M, Galand A, and Vrensen G F. Exp Eye Res. 2000 November; 71(5): 489-94. LECs and CEDCs are cultured in Eagle's minimum essential medium (MEM). RPECs are cultured in Ham's F10 medium, supplemented with 2 mM glutamine, 25 mmol/L Hepes, pH 7.4, 10 U/mL penicillin, and 10 µg/mL streptomycin and 15% heat-inactivated foetal cow serum (FCS). The primary cultured LECs, CEDCs, and RPECs are sub-cultured at $10^4$ cells/wells in 96-well flat-bottom plates until they reached 90 to 100% confluence. These cells are grown to confluence in an incubator with a humidified atmosphere of 5% $CO_2$ at 37° C. The cells are kept in a confluent state for overnight before assays.

Hyperosmotic solutions of NaCl are prepared by first making a 2 M NaCl stock solution by adding 58.44 grams of NaCl to 500 ml $dH_2O$ (NaCl supplied by Sigma Chemical co, Dorset, England). A desired concentration of osmotic NaCl solution is then prepared by diluting the 2M stock solution with distilled water ($dH_2O$). For example, to make a hyperosmotic solution of 170 mM NaCl, the 2M NaCl stock solution is diluted with $dH_2O$ at a ratio of 1 to 10.1; to make a hyperosmotic solution of 340 mM NaCl, the 2M NaCl stock solution is diluted with $dH_2O$ at a ratio of 1 to 4.56. Final osmolarities ($mOsm/kg/H_2O$) are determined by a freezing point depression method using a Cryoscopic Osmometry.

After treatment, the treated cells are thoroughly washed, and cultured with fresh media for twelve hours before cell viability is assessed. The capability of these cells to survive at the indicated hypertonic stress levels is assessed by an MTT assay 12-24 hours post-exposure.

MTT assay is an assay to assess mitochondria function, performed as described by Mosmann (Mosmann, T. J Immunol Methods. 1983 Dec. 16; 65(1-2): 55-63. The tetrazolium salt 3-(4,5-dimethylthiazol-2-yl)-2,5-diphenyl tetrazolium bromide (MTT; supplied by Sigma Chemical Co.) is dissolved in Phosphate's Balanced Salt (PBS) Solutions at 5 mg/ml and sterilized by passage through a 0.22 µm Millipore filter. MTT stock solution is added to growth media at a ratio of 1 to 10. Cells are incubated with this growth media for three to four hours. In cells that are alive at the time of adding MTT, mitochondrial dehydrogenase cleaves the tetrazolium ring into a dark blue formazan reaction product, which builds up in the cell. MTT-reacted cultures are observed under brightfield microscopy without further processing. Cells in each well are scored as MTT-positive if they are completely filled with reaction product (in the case of unattached cells) or contain many formazan crystals emanating from multiple foci (in the case of attached or spread cells). MTT-reacted cultures are then lysised by dimethyl sulfoxide (DMSO) and read in a Microplate Reader to obtain a measure of cell viability. The number of live cells (MTT-positive) per well is determined at the specified concentrations and expressed as a percentage of total cells (demonstrated in FIG. 1).

Example 2

Confluent monolayers of LECs are given three washes with Hank's Balanced Salt Solutions (HBSS) to remove FCS before the experiment. LECs are prepared in 96-well culture plates as in Example 1. These cells are exposed for about five to ten minutes to 200 µl/well of treatment solutions comprising increasing concentrations (~135 mM, ~170 mM, ~340 mM, ~680 mM, ~1360 mM and ~2000 mM) of NaCl (an osmolyte) in the presence and the absence of 30 µM frusemide (a co-transport interference agent, an ion transport mechanism interference agent). The treatment solutions have a pH of 8.0±0.4. After treatment, the treated cells are thoroughly washed, and cultured with fresh media. The viability of the treated LECs was determined by MTT assay 12-24 hours post-treatment as described in Example 1.

Figure 2:
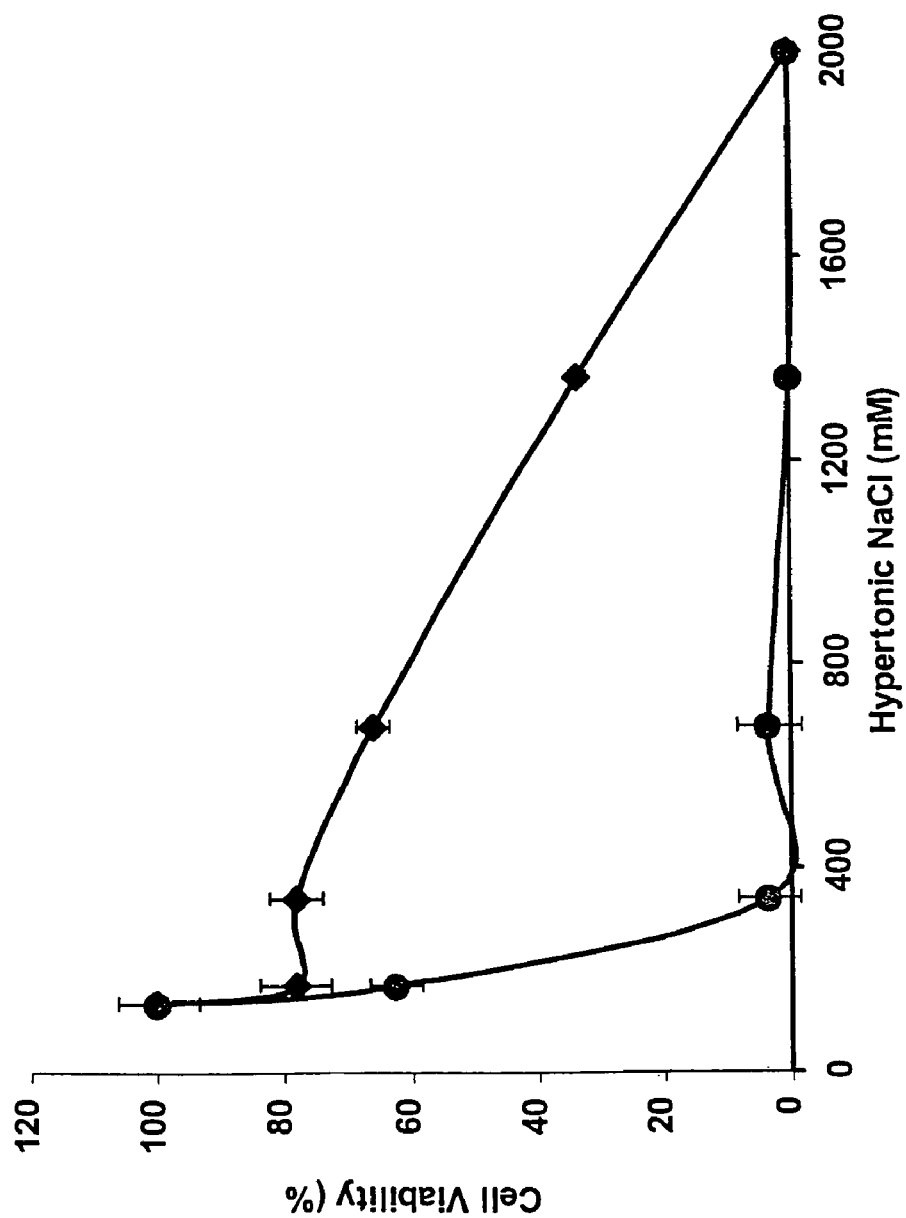
FIG. 2 is a diagram illustrating cell viabilities of LECs after application of increasing concentrations of NaCl in the absence (diamonds) and the presence (circles) of 30 µM frusemide, a co-transport interference agent.

After this treatment, the same phenomenon of cell shrinkage and detachment as observed in Comparative Example 1 also occurs in the presence of frusemide, but the changes are much more dramatic. FIG. 2 shows that in the absence of frusemide (depicted in diamonds) about 40% of LECs survive after a rapid hypertonic shock with 1380 mM NaCl. However, after inhibition of co-transport mechanisms using frusemide (depicted in circles), the osmotic tolerance of LECs is dramatically reduced, and almost no cells survive after rapid hypertonic shock with 340 mM NaCl. This result shows survival capability of the LECs shifts from hypertonic shock with 200 mM NaCl in the absent of frusemide to 170 mM NaCl in the presence of the frusemide.

Each point represents the mean±standard deviation (S.D) of three experiments. A stock solution of 30.3 mM frusemide is prepared by first dissolving 20 mg frusemide in 100 µl DMSO to make sure it dissolved and then adding it to 1.9 ml of the desired concentration of hyperosmotic NaCl. To get 30 µM frusemide, five µL of frusemide stock solution is then added to five ml of the desired concentration of NaCl solution (which is prepared as described in Comparative Example 1).

Comparative Example 3

This example demonstrates effects of pH on LECs osmotic survival. Confluent monolayers of the LECs are prepared as described in Comparative Example 1. A control group of cells are exposed to a solution comprising physiological 135 mM NaCl at a pH of 7.4±0.3. A different group of cells are exposed for ten minutes to 200 µl/well of the solutions comprising increasing concentrations of NaCl (~170 mM, and 340 mM) at varying pH (8.0±0.4, 8.4±0.5, 8.9±0.8, and 10.6±0.5).

The pH of the solutions is adjusted by directly adding 0, 1, 3, or 5 µl of 5N NaOH stock solution to 10 ml of the selected hyperosmotic NaCl solutions (which are prepared as described in Example 1). The corresponding final pH was determined by using a professional pH metre. Final pH in 10 ml of the NaCl solution without addition of NaOH gave a reading of pH about 8.0±0.4. Final pH in 10 ml of the NaCl solution with 1 µl of 5N NaOH gave a pH reading of about 8.4±0.5. Final pH in 10 ml of the NaCl solution with 3 µl of 5N NaOH gave a pH reading of about 8.9±0.8. Final pH in 10 ml of the NaCl solution with 5 µl of 5N NaOH gave a reading of about 10.6±0.5.

Figure 3:
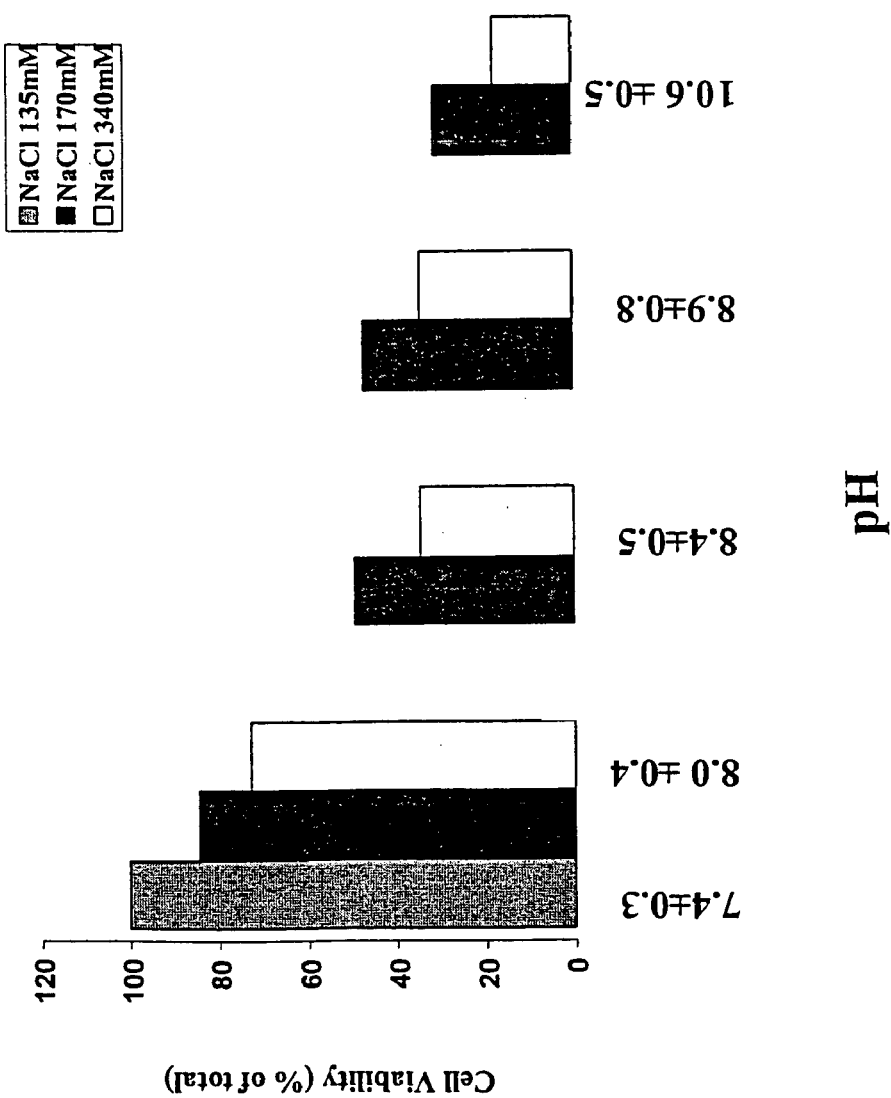
FIG. 3 is a diagram illustrating cell viabilities of total LECs after application of the solutions comprising increasing concentrations of NaCl at varying pH levels.

Cell viability of the treated cells is determined by MTT assay 12-24 hours post-treatment as described in Example 1. Cell viability of LECs after application of solutions is depicted in FIG. 3. As shown, the gray bar represents the control group in which LECs were exposed to physiological 135 mM NaCl. The black and white bars represent the LECs exposed to 170 mM NaCl and 340 mM NaCl, respectively, with increasing pH. As shown, LECs sensitivity to hypertonic stress increases with increasing pH and increasing NaCl concentrations. At pH of about 10.6±0.5, about greater than seventy five percent of LECs burst and die within five minutes. At pH of about 8.9±0.8, the LECs detach effectively from their substrates but do not burst significantly.

Comparative Example 4

This example demonstrates effects of extracellular pH on the RPECs osmotic survival. Confluent monolayers of RPECs are prepared as described in Example 1. These cells are exposed for ten minutes to 200 µl/well of the solutions comprising increasing concentrations of NaCl (137 mM, 170 mM, 340 mM, 680 mM, 1360 mM and 2000 mM) at varying pH (8.4±0.5 and 10.6±0.5). The solutions of NaCl are prepared as described in Example 1. The pH of the solutions is adjusted with additions of 1 µl and 5 µl of 5N NaOH as described Example 3.

Figure 4:
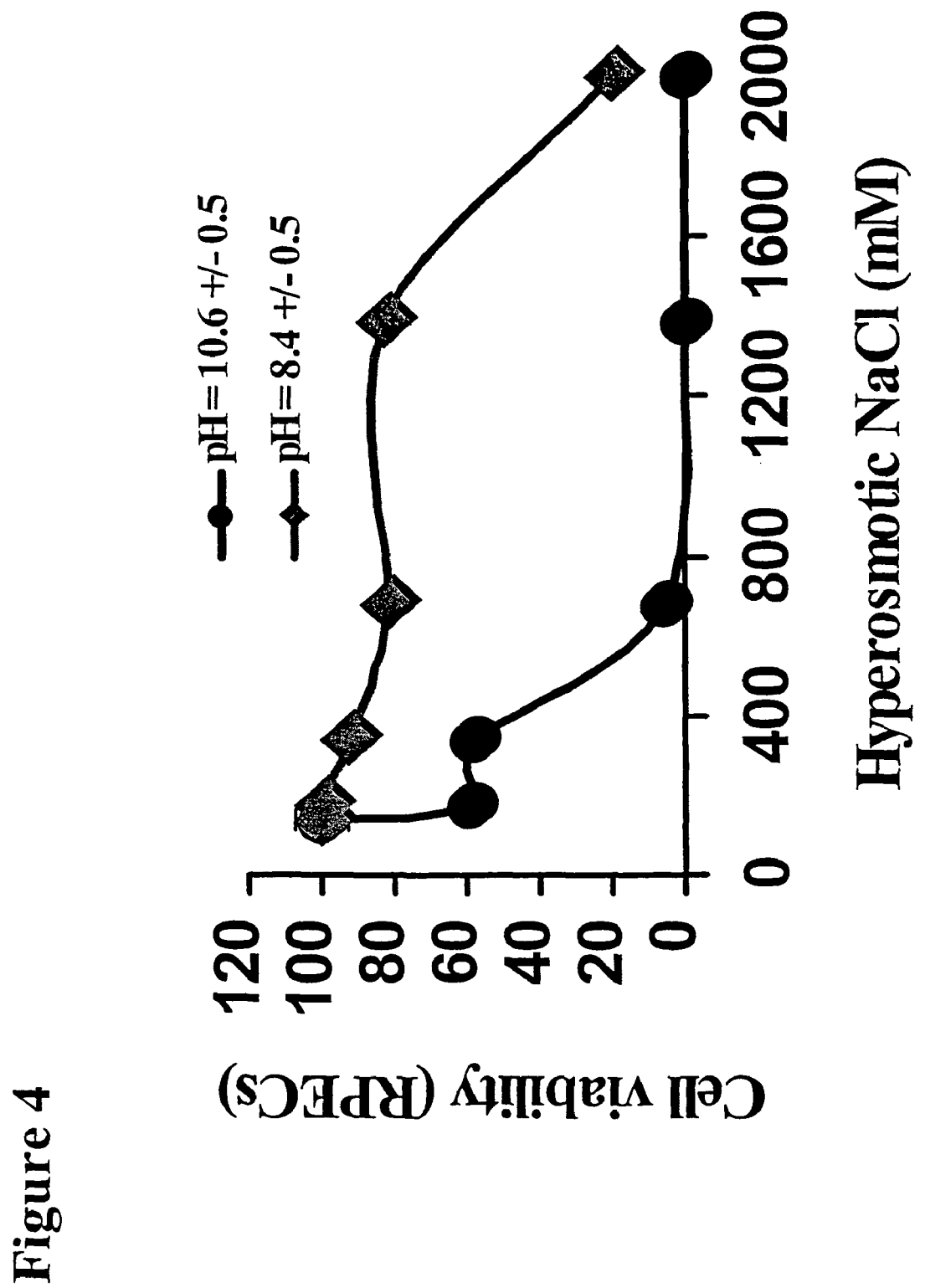
FIG. 4 is a diagram illustrating cell viabilities of RPECs after application of solutions comprising increasing concentrations of NaCl at varying pH levels.

The viability of the treated cells was determined by MTT assay 12 to 24 hours post-treatment as described in Example 1. Cell viability of RPECs after application of the solutions is depicted in FIG. 4 (pH 8.4±0.5 depicted in diamonds; pH 10.6±0.5 depicted in circles). Each point represents the mean±standard deviation of three experiments. As shown, there is a dramatic decrease in the survival level of RPECs exposed to hypertonic NaCl when the pH level is raised.

Example 5

Confluent monolayers of LECs and RPECs are prepared as described in Example 1. These cells are exposed for about ten minutes to 200 µl/well of treatment solutions comprising: (i) ≦200 mM hyperosmotic NaCl; (ii) increasing concentrations (10 µM, 30 µM, 60 µM, 90 µM, and 120 µM) of co-transport interference agent, frusemide, and (iii) 3 µl of 5N NaOH.

The treatment solutions containing frusemide are prepared as described in Example 2, by diluting stock solution of frusemide with ≦200 mM hyperosmotic NaCl solution (prepared as described in Example 1). For example, to get a hyperosmotic NaCl solution with 60 µM frusemide, 10 µL of frusemide stock solution is added to 5 mL hyperosmotic NaCl solution. The pH of the solutions is adjusted with 3 µl of 5N NaOH.

Figure 5:
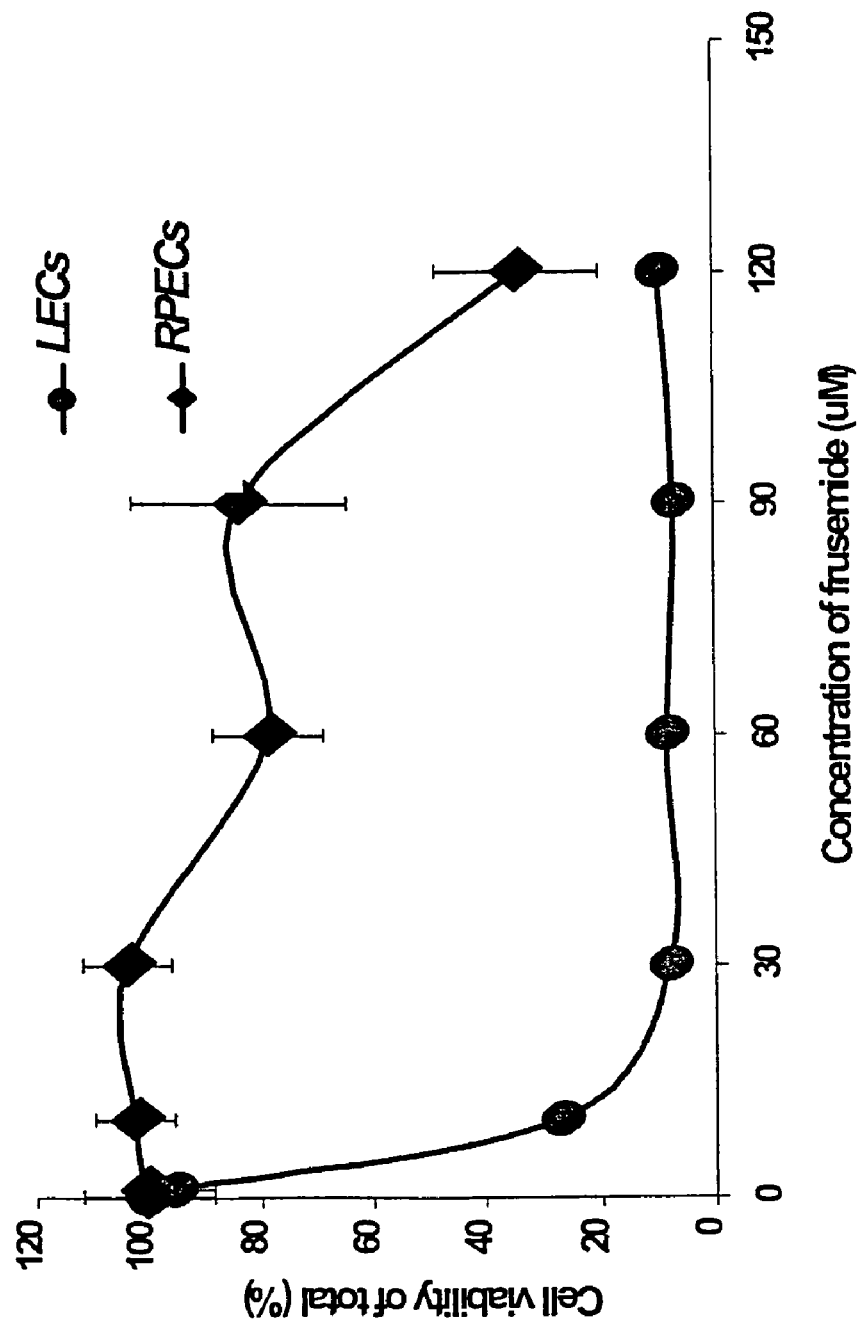
FIG. 5 is a diagram illustrating cell viabilities of LECs and RPECs after application of treatment solutions comprising ≦200 mM NaCl, increasing concentrations of a co-transport interference agent, frusemide, and 3 µl of 5N NaOH.

The viability of the treated cells is determined by MTT assay 12 to 24 hours post-treatment as described in Example 1. Cell viability of LECs (circles) and RPECs (diamonds) are depicted in FIG. 5. Each point represents the mean±standard error (s.e.m) of six experiments for the HLECs and four experiments for the HRPECs. As shown, at 10 µM frusemide, more than 50% of the LECs shrink, are lost or die. Between 30 µM and 120 µM frusemide, about >90% of LECs are removed or killed. On the other hand, between 30 µM and 90 µM frusemide, few RPECs are removed or killed. Therefore, for example, in about 200 mM hyperosmotic NaCl solution at this pH, about 15 µM to about 100 µM are effective concentrations at which no significant harm was done to RPECs.

Example 6

Confluent monolayers of LECs, CEDCs and RPECs are prepared as described in Example 1. These cells are exposed for about ten minutes to 200 µl/well of treatment solutions comprising: (i) ≦200 mM hyperosmotic NaCl, (ii) increasing concentrations (14 µM, 28 µM, 56 µM, 112 µM, and 224 µM) of bumetanide, a co-transport interference agent, and (iii) 3 µl of 5N NaOH.

The treatment solutions containing Bumetanide are prepared as follows. A stock solution of 1.4 M bumetanide is prepared. A second stock solution of 14 mM bumetanide is then made by diluting 1 µL of the 1.4 M bumetanide solution with 1 mL hyperosmotic NaCl solution (prepared as described in Example 1). The final desired concentrations of bumetanide are obtained by diluting the 14 mM bumetanide stock solution with NaCl solution to get concentrations of approximately 0 M (control) 14 µM, 28 µM, 56 µM, 112 µM, and 224 µM, respectively. The pH of the solutions is adjusted with 3 µL of 5 N NaOH.

Figure 6:
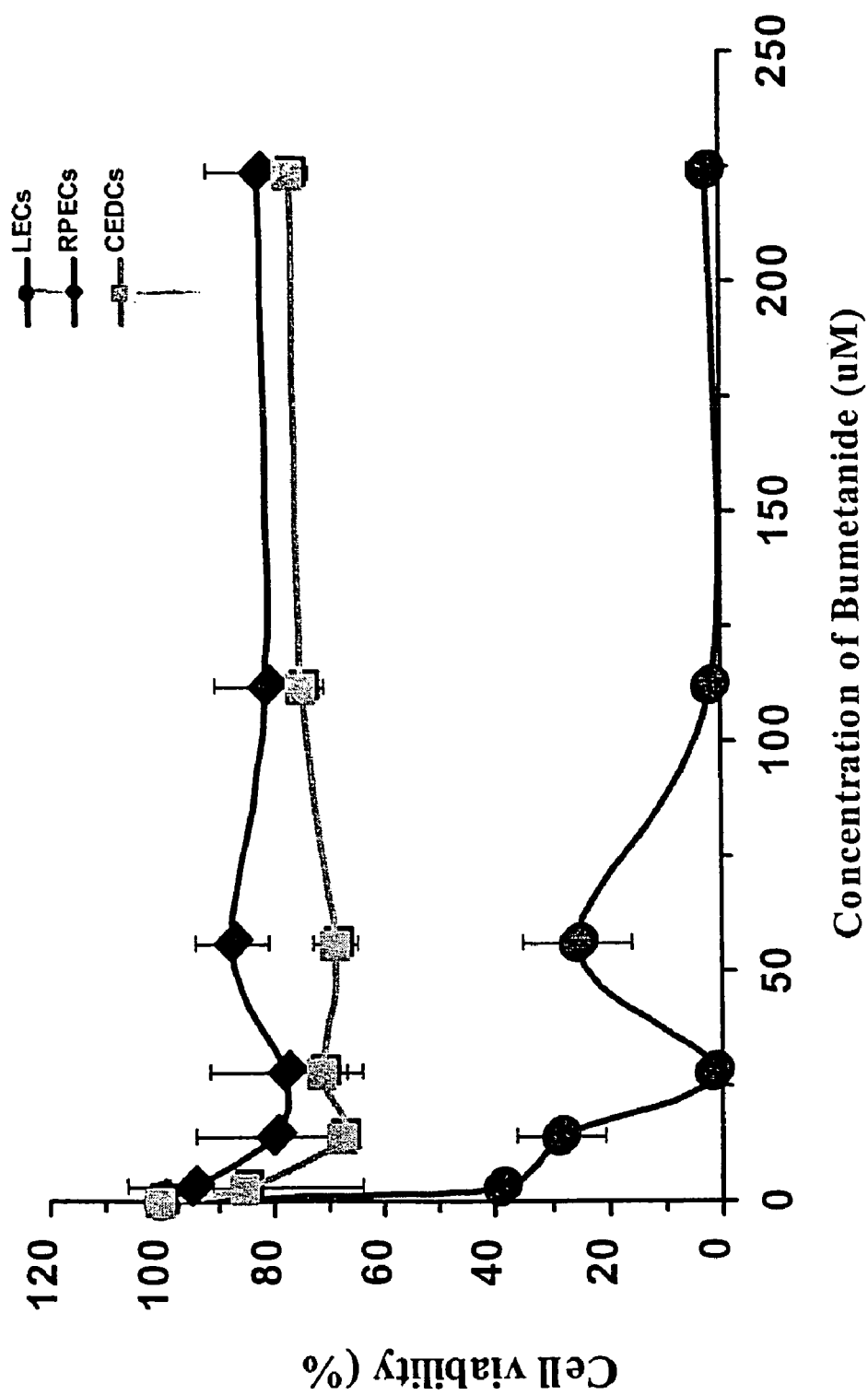
FIG. 6 is a diagram illustrating cell viabilities of LECs, RPECs, and CEDCs after application of treatment solutions comprising ≦200 mM NaCl, increasing concentrations of a co-transport interference agent, bumetanide, and 3 µl of 5N NaOH.

The viability of the treated cells was determined by MTT assay 12 to 24 hours post-treatment as described in Example 1. FIG. 6 depicts cell viability of LECs (circles), RPECs (diamonds) and CEDCs (squares). Each point represents the mean±s.e.m and standard deviations of six experiments for LECs and three experiments for RPECs and CEDCs, respectively. As shown, at 28 µM, 112 µM, and 224 µM bumetanide, nearly all of the LECs shrink, detach and/or die under phase-contrast microscopic observation, and there are almost no cells left after washing. Nearly 100% cells show MTT negative response. On the other hand, at these same concentrations, less than about 20% RPECs and 30% CEDCs are killed or removed. Accordingly, 28 µM, 112 µM, and 224 µM bumetanide are suitable therapeutic concentrations for these particular treatment solutions.

Example 7

Confluent monolayers of LECs are prepared as described in Example 1 and grown on a glass cover-slip instead of 96-well flat bottom culture plates. The LECs are then thoroughly washed to remove serum.

Ten milliliters (10 mL) of the treatment solution containing ≦200 mM NaCl, 90 µM frusemide and 3 µl of 5N NaOH is prepared in a deep 35 mm petri-dish.

The cover-slips are then transferred to the petri-dish containing the treatment solution and are kept in the treatment solution for five to ten minutes. The treatment solution is then poured away, and the cover-slips along with detached LECs are thoroughly rinsed with a fresh HBSS solution with slight pressure using an aspiration/irrigation probe. After immediate examination and photography using inverted phase contrast microscope, the LECs are kept in culture for seven days with fresh medium to examine whether any residual cells would survive.

Figure 7:
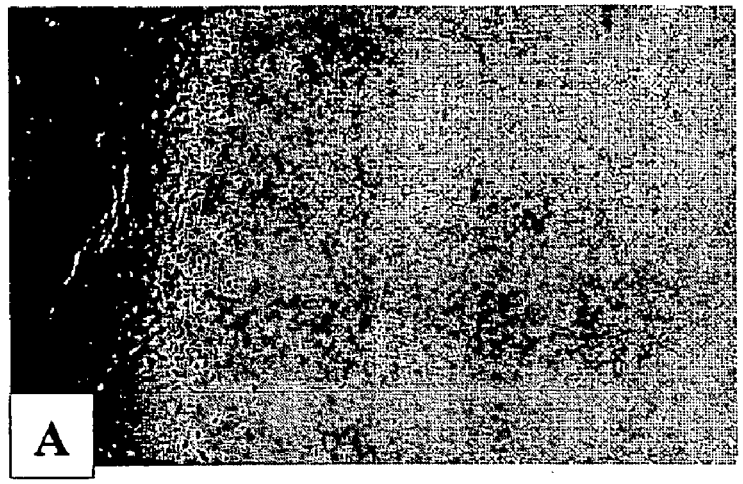
FIG. 7 is three photographs illustrating the effects of treatment on primary cultured LECs with the treatment solutions of the present invention at (A) zero, (B) five and (C) ten minutes after washing.
Figure 7:
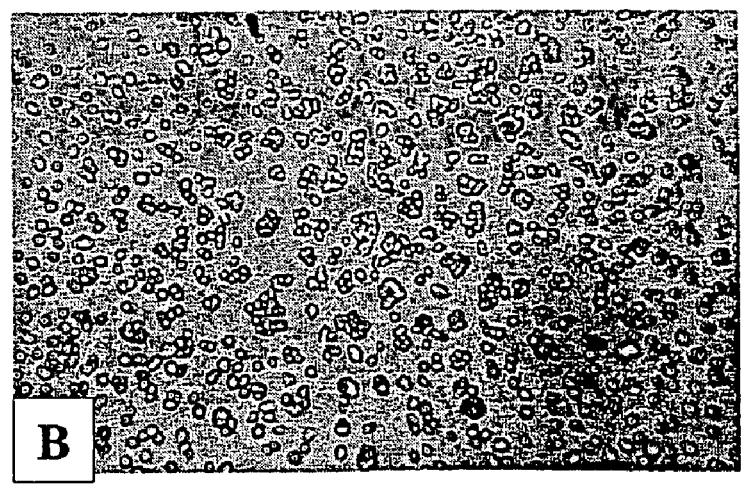
Figure 7:
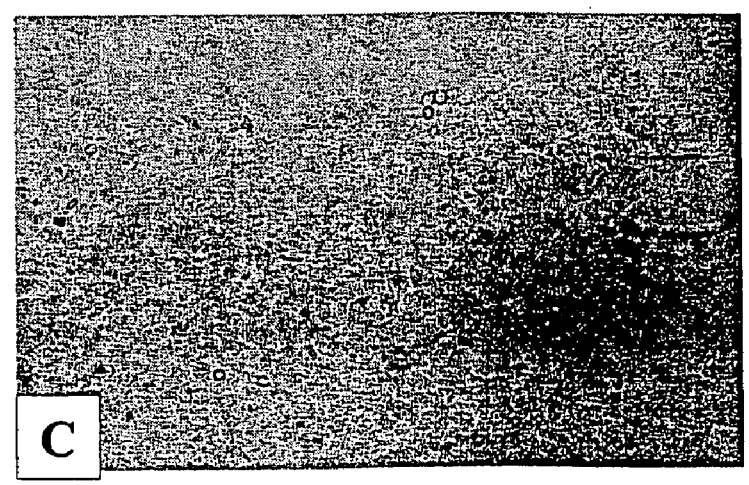

FIG. 7 depicts images of LECs taken using an inverted phase-contrast microscope and their osmotic responses during treatment. Photograph 7A depicts, at zero minutes, confluent LECs covering the entire area. Photograph 7B depicts, at five minutes post-treatment, the LECs rounded up and separating from their substrate. Photograph 7C depicts, at ten minutes post-treatment and after washing, a substantially clear substrate after the cells have been washed away.

Example 8

In order to assess the effects of the therapy in an environment close to that in vivo, a lens organ culture PCO model is used (model was originally developed by Liu et al (Liu C S, Wormstone I M, Duncan G, Marcantonio J M, Webb S F, Davies, P D. Invest Ophthalmol Vis Sci. 1996 April; 37 (5): 906-14). Human lenses are isolated from donor eyes (ages between 19 to 89 years), and then glued onto a tailor-made stainless steel stand. Under an operating microscope, the anterior portion of the lens capsule 100, which is about 6 mm in diameter, is carefully opened using the technique of continuous curvilinear capsulorhexis. The lens nucleus is then hydroexpressed with HBSS and the remaining lens fibres carefully removed. The posterior capsule 200 and equatorial capsule 300 are left intact as envelopes (bags), stored in plastic culture dishes (deep 35 mm petri-dish) and covered with Eagle's Minimum Essential Medium growth medium (MEM) supplemented with 10% to 15% FCS. The human LECs in the organ culture model are then allowed four to five days to recover from the surgical trauma.

Two groups of organ cultured PCO models were established. The first group of ten lenses was established as a control and kept in organ culture without treatment. All of these lenses developed confluent mono- or multiple-layered proliferated LECs on the anterior capsule 100 and posterior capsule 200 after about four to seven days.

The second group of twenty lenses, after four to five days of culture, also had a monolayer of the proliferated LECs. This group was thoroughly washed to remove serum prior to the introduction of the treatment solutions. Ten milliliters (10 mL) of treatment solutions comprising: (i) ≦200 mM NaCl, (ii) about 90 µM frusemide, or about 28 µM bumetanide, or about 112 µM bumetanide, and (iii) 3 µl of 5N NaOH are prepared in a deep 35 mm petri-dish. The solutions are prepared as described in other examples. The organ cultures are then transferred to the petri-dish containing the treatment solutions and are kept in the treatment solution for five to ten minutes. The organ cultures are then transferred using forceps into another petri-dish. The capsules along with detached LECs in the PCO organ culture are then thoroughly rinsed with a fresh HBSS solution with slight pressure using an aspiration/irrigation probe. After immediate examination, the organ cultures are kept in culture for seven days with fresh medium to examine whether any residual cells would survive.

Figure 8:
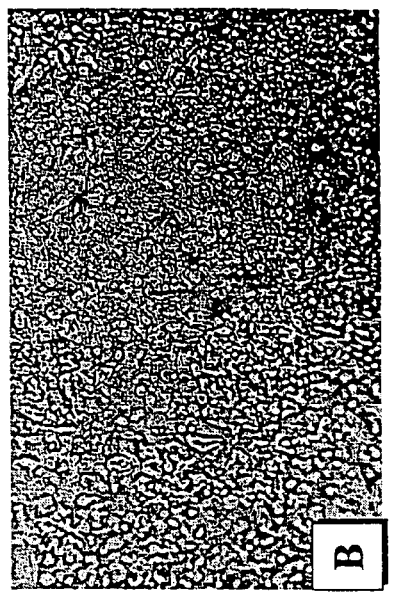
FIG. 8 is four photographs illustrating the effects of treatment on primary LECs in a human organ culture PCO model with the treatment solutions of the present invention (A) before treatment, (B) five minutes after treatment, (C) ten minutes after treatment, and (D) after washing.
Figure 8:
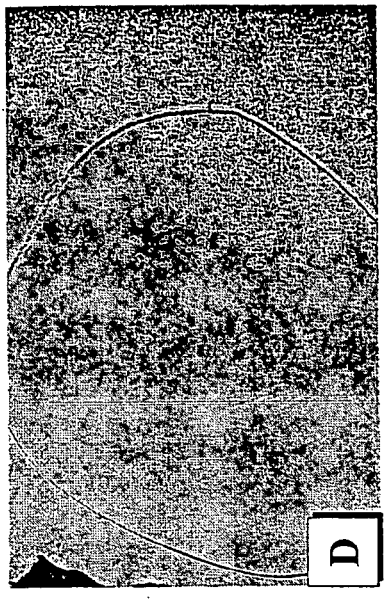
Figure 8:
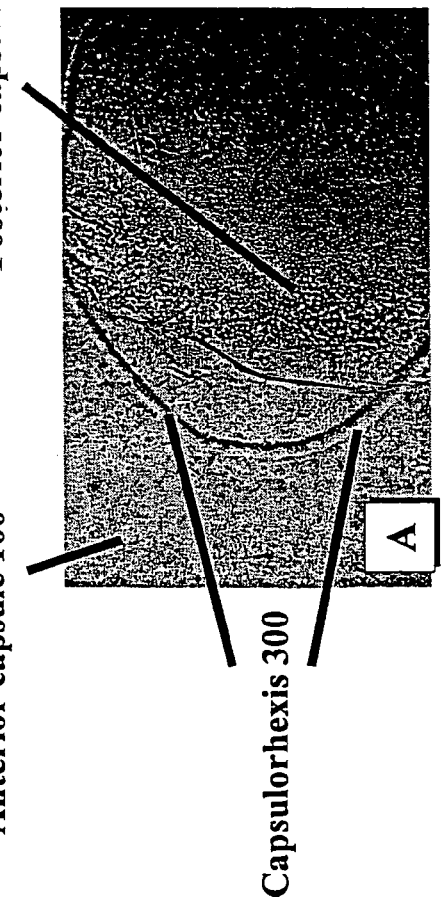
Figure 8:
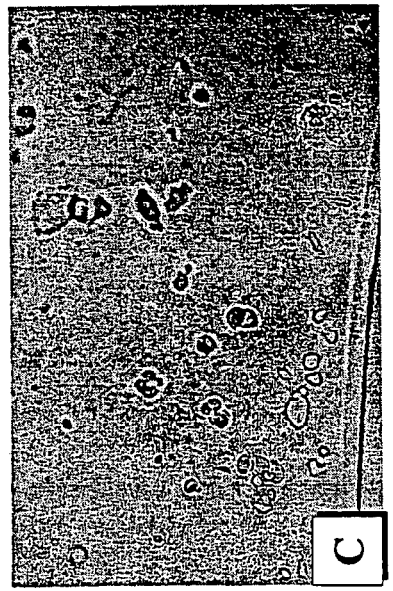

The effect of this treatment on LECs in PCO organ culture model is examined on inverted microscope using phase contrast optics. They are photographed with T-Max 400 film (Kodak) at zero, five, and ten minutes and at twelve hours post-treatment. As shown in FIG. 8, within five to ten minutes of treatment, all of the LECs round up and lose adhesion from the monolayer and the lens capsule. Phase contrast micrograph 8A depicts at low magnification (field of view is 1 mm×0.75 mm) the proliferated LECs after a sham ECCE operation on the anterior 100 and posterior capsule 200 six to seven days after dissection and before treatment. Phase contrast micrograph 8B depicts at high magnification (field of view is 3.4 mm×1.5 mm) the LECs starting to round up and detach from the lens capsule five minutes after treatment. Phase contrast micrograph 8C depicts at high magnification the majority of treated cells detached from the monolayer ten minutes after treatment. Phase contrast micrograph 8D depicts at low magnification that, after washing, the lens capsule was devoid of LECs ten minutes after treatment.

Example 9

In this example, the effects of the treatment on primary RPECs are examined. To assess whether there are any side effects on other ocular cells, the primary cultured RPECs were cultured in 6-well flat-bottom culture plate until they reached 90 to 100% confluence in Ham's F10 medium, supplemented with 2 mM glutamine, 25 mmol/L Hepes, pH 7.4, 10 U/mL penicillin, and 10 μg/mL streptomycin and 15% heat-inactivated foetal cow serum (FCS). The cultures were kept in an incubator with a humidified atmosphere of 5% $CO_2$ at 37° C. and were kept in a confluent state for overnight before assays.

The RPEC cultures were thoroughly washed to remove serum prior to the introduction of the treatment solutions. Twenty milliliters (20 mL) of the treatment solution comprising (i) ≦200 mM NaCl, (ii) about 90 μM frusemide, or about 28 μM bumetanide, or about 112 μM bumetanide, and (iii) 6 μl of 5N NaOH is prepared in a deep 35 mm petri-dish as described in previous examples. Five milliliters (5 ml) of the treatment solution is then added to the confluenced RPECs in each well of 3 wells in a 6-well culture plate. After about 10 minutes, the solution is removed completely and the treated RPECs are thoroughly rinsed with a fresh HBSS solution with slight pressure using an aspiration/irrigation probe. After immediate examination, the primary RPEC cultures are kept in culture for seven days with fresh medium to examine whether any residual cells would survive.

Figure 9:
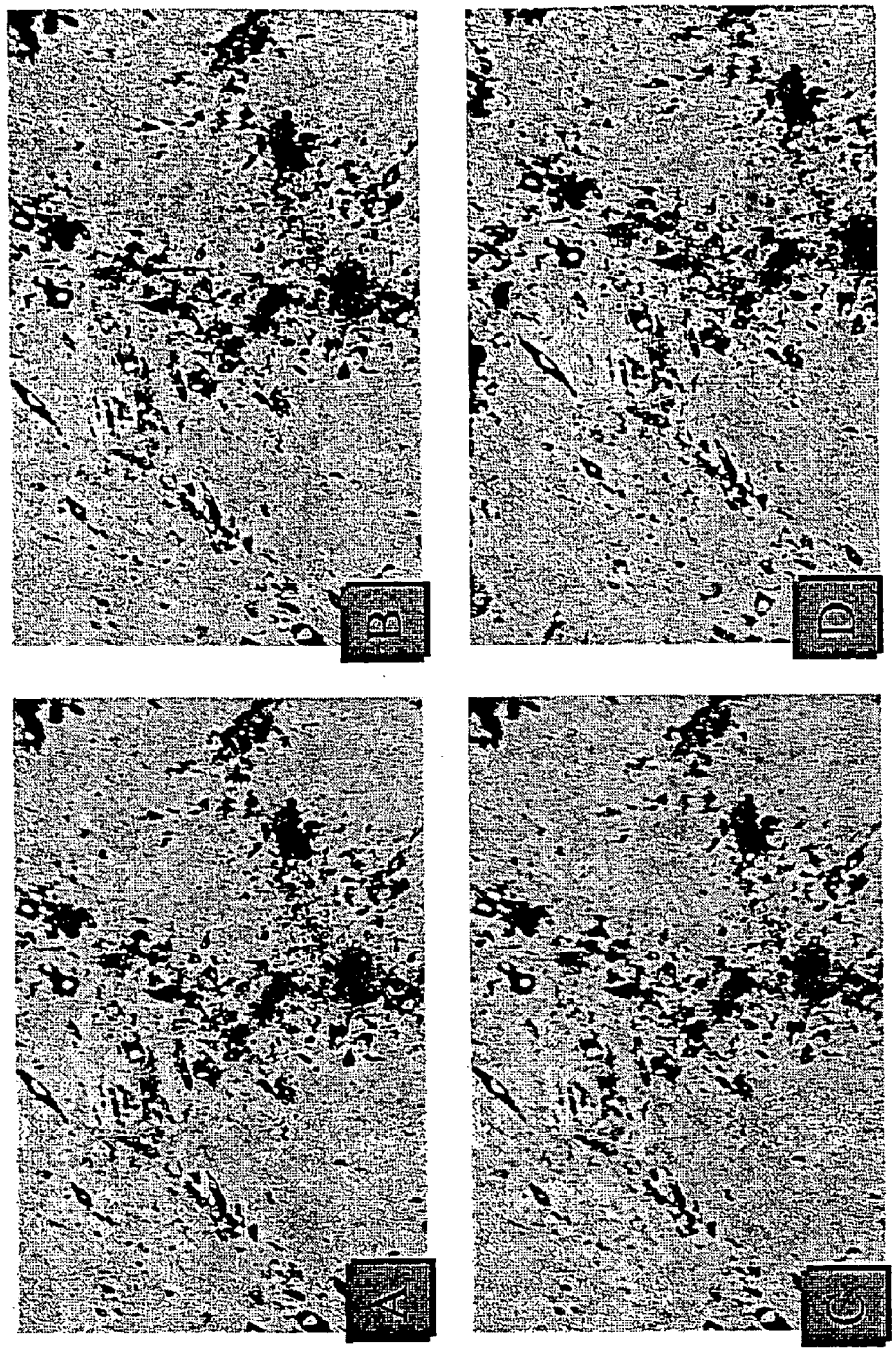
FIG. 9 is four photographs illustrating the effects of treatment on RPECs with a treatment solution comprising ≦200 mM NaCl, 90 μM frusemide, and 3 μl of 5N NaOH at (A) zero, (B) five, and (C) ten minutes post-treatment and (D) after washing.

The effect of treatment on these primary RPECs are examined on inverted microscope using phase contrast optics. They are photographed with T-Max 400 film (Kodak) at zero, five, and ten minutes and at twelve hours post-treatment. The RPECs are not significantly affected by ten minutes exposure to the treatment solutions. FIG. 9 depicts a representative example of the effects of the treatment on these cells. Photograph 9A depicts RPECs at zero minutes. Photograph 9B depicts RPECs at five minutes posttreatment. Photograph 9C depicts RPECs ten minutes post-treatment. Photograph 8D depicts RPECs after the cells were washed following treatment.

Example 10

To assess whether there is any side effect of this treatment on other ocular cells, confluent monolayers of LECs, CEDCs and RPECs are prepared as described in Example 1. These cells were exposed for about ten minutes to 200 μl/well of treatment solutions comprising ≧200 mM NaCl, 90 μM frusemide, and 3 μl of 5N NaOH.

Figure 10:
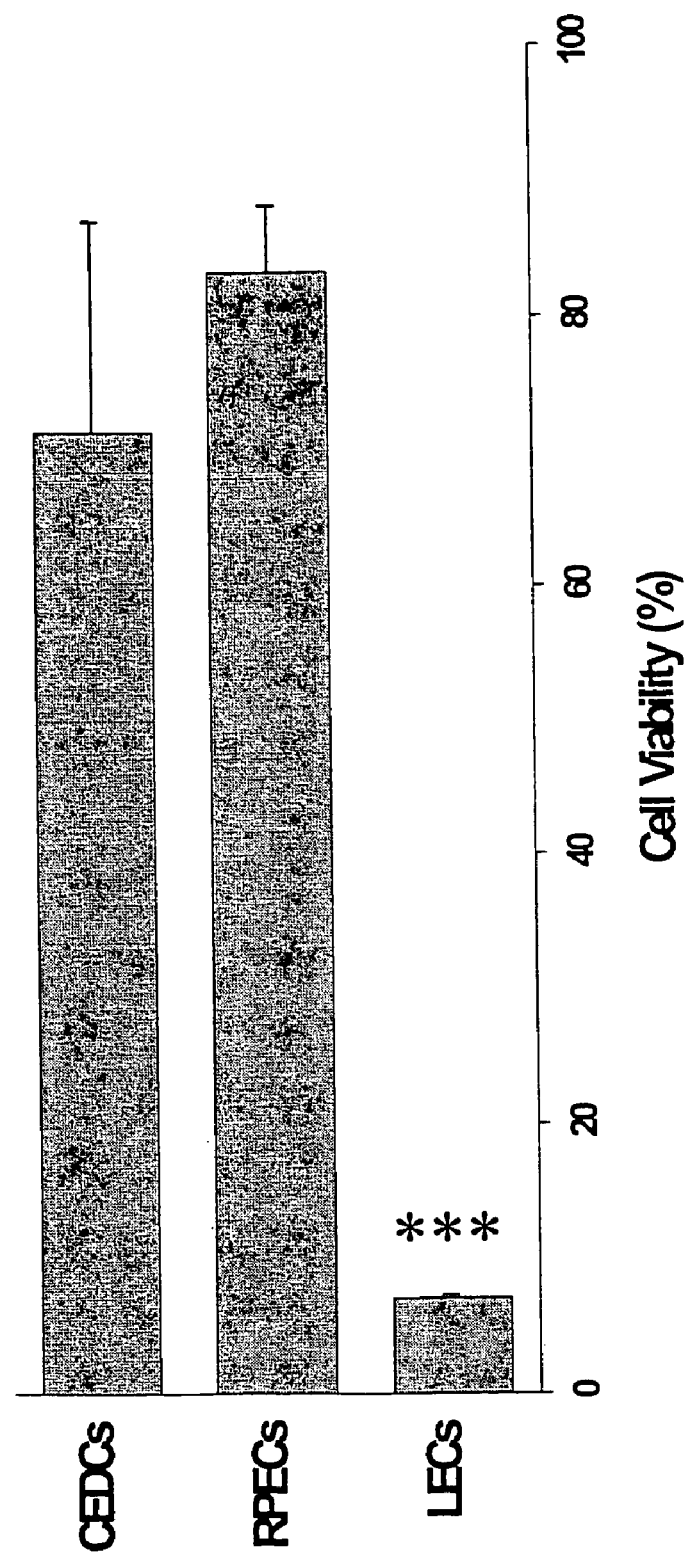
FIG. 10 is a diagram illustrating cell viabilities of LECs, RPECs and CEDCs after application of treatment solutions comprising ≦200 mM NaCl, 90 μM frusemide and 3 μl of 5N NaOH.

The viability of the treated cells was determined by MTT assay 12 to 24 hours post-treatment as described in Example 1. Cell survival response of LECs, RPECs and CEDCs to the treatment are depicted in FIG. 10. Each point represents the mean±s.e.m. of four experiments. As shown, ten minutes after treatment, the treatment solution induced substantially greater incidence of cell detachment and/or death, measured by cell viability, of LECs than CEDCs and RPECs. Specifically, more than seventy percent of CEDCs and eighty percent of RPECs survived after the treatment. This can be compared to a less than ten percent survival rate for LECs.

Example 11

The effects of treatment on organ cultured corneal buttons is examined to determine whether the treatment would cause damage to surrounding ocular tissues in an environment close to in vivo. Cornea is chosen because of its sensitivity and the danger of direct exposure to treatment. Corneal organ cultures are washed with HBSS and placed endothelial-side up on a tailor-made stainless steel stand. They are then stored in a sterile culture dish containing MEM growth medium covering only the bottom of the culture dish, providing a humidified chamber to prevent drying of the epithelium. The endothelial corneal concavity is then filled with MEM growth medium supplemented with 10% to 15% FCS, and cultured at 37° C. in a 5% $CO_2$ incubator.

The organ cultures are divided into control and treatment groups. The cultures are first washed three times with HBSS and then their endothelial surfaces are exposed for ten minutes to either physiological NaCl (137 mM, 293±9 mOsm/L) or the treatment solution.

For the treatment group, ten milliliters (10 mL) of treatment solutions comprising (i) ≦200 mM NaCl, (ii) about 90 μM frusemide or about 112 μM bumetanide, and (iii) 3 μl of 5N NaOH are prepared in a deep 35 mm petri-dish. The organ cultures are transferred to the petri-dish containing the treatment solution and are kept in the treatment solution for more than ten minutes. The organ cultures are then transferred using forceps to another petri-dish containing fresh HBSS. The corneal organ cultures are then thoroughly rinsed with a fresh HBSS solution with slight pressure using an aspiration/irrigation probe. After the treatment, the corneal organ culture is incubated in fresh medium for six hours.

For the control group, instead of the treatment solution described above, a fresh HBSS was applied to the corneal organ cultures for ten minutes.

To assess toxicity of the treatment on corneal endothelial cells, the corneal organ culture buttons are examined by both inverted microscope using phase contrast optics and fluorescent-confocal microscopy. Under confocal microscope, the morphology of actin filaments of corneal endothelial cells is examined to establish evidence for the intact architecture of the cells. The endothelium of these corneal organ cultures is fixed before and after treatment, and stained with FITC-conjugated phalloidin. Confocal laser-scanning images of corneal endothelium demonstrate no significant differences between untreated (control) and treated groups. The endothelial sheet in the treated group maintains the same integrity as those in the untreated group. The corneal endothelial cells remain as an evenly distributed monolayer with the cells keeping their hexagonal appearance in the control as well as in the treated organ cultures. There is no apparent damage to corneal endothelium cells.

Example 12

The in situ effects of a treatment solution comprising dihydrochlorothiazide (DHCT) (a cotransport interference agent from the group of the thiazide and related diuretics) and hyperosmotic NaCl on human LECs is examined. The treatment is tested on LECs that are still attached to a continuous curvilinear capsulorhexis lens capsule (LECs-CCC) which are freshly removed from a human cataract operation.

The LECs-CCCs are obtained from a cataract operation and immediately put in freshly prepared Eagle's Minimum Essential Medium (MEM) supplemented with 2 mM glutamine, 25 mmol/L Hepes (pH 7.4) without foetal cow serum (FCS) and is transferred to the laboratory for evaluation. Viable LECs are identified by staining the LECs-CCCs for five minutes with 0.2% Trypan Blue. The sheets containing more than 70% viable LECs are used to assess the efficacy of the treatment.

The treatment solutions are composed of either 170 or 200 mM NaCl in $dH_2O$ and 200 or 300 μm DHCT.

In the first step, a hyperosmotic solution of NaCl is prepared by making a stock solution of 2 M NaCl by adding 58.44 g NaCl (supplied by Sigma Chemical Co., U.S.) to 500 ml $dH_2O$. The desired concentration of osmotic NaCl is prepared by diluting the 2M stock solution with $dH_2O$. For example, to make a hyperosmotic solution of 170 mM NaCl, the 2M NaCl stock solution was diluted with $dH_2O$ at a ratio of 1 to 10.1. To make a hyperosmotic solution of 200 mM NaCl, the 2M NaCl stock solution is diluted with $dH_2O$ at a ratio of 1 to 9. Final osmolarities (mOsm/kg/$H_2O$) are determined by a freezing point depression method using cryoscopic osmometry.

In the second step, DHCT stock solution is made by adding 25 mg DHCT to 1 ml $dH_2O$.

In the final step, the treatment solution with 200 or 300 μm DHCT is made by diluting the DHCT stock solution in the 170 mM or 200 mM hyperosmotic NaCl and the pH is adjusted to ±7.8.

The treatment is applied by exposing the LECs-CCCs for five minutes in a small petri dish containing the treatment solution. The treatment solution is removed after five minutes exposure by a syringe and then the fresh PBS is added in the petri dish to wash away the treatment solution. The LECs-CCCs are washed three times. The changes of the LECS are monitored under a microscope. Microscope photographs are taken at 0, 2 and 5 minutes and after wash.

After exposure to the treatment solution, the human LECs shrink and gradually large gaps form between the cells. The shrinking cells then gradually round up and burst.

Figure 11:
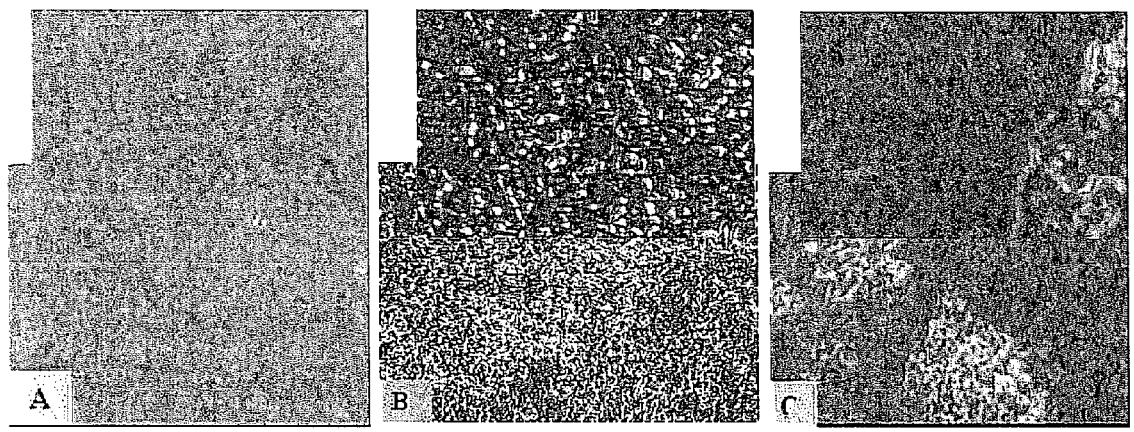
FIG. 11 is photographs illustrating the effects of treatment on LECs-CCCs with a treatment solution containing 200 μM DHCT and hyperosmotic ≦200 mM NaCl at (A) zero minutes, (B) about two minutes and (C) after wash.

FIG. 11 shows changes of LECs-CCCs caused by a treatment solution containing 200 μm DHCT and hyperosmotic≦200 mM NaCl at (A) zero minutes, (B) two to three minutes and (C) after wash. In FIG. 11A, which shows the lens cells before treatment, the lens cells are tightly packed and in close contact with adjacent cells and resemble an intact sheet. The inset in FIG. 11A is a higher magnification of the image. FIG. 11B, taken two to three minutes post-treatment, shows the cells shrinking with large gaps between cells. The inset in FIG. 11B is a higher magnification of the image. In FIG. 11C, taken after rinsing away the treatment solution and the detached cells, no living cells can be observed aside from some remaining cell debris. The inset in FIG. 11C is a higher magnification of the image.

Example 13

The in vivo efficacy of the treatment described in Example 12 on the prevention of PCO is examined by experiments on two groups of New Zealand albino rabbits. The experimental group includes sixteen rabbit eyes and the control group includes four rabbit eyes. A sham cataract operation is performed on the control animals. The therapy is introduced to the others.

The pupil of each rabbit eye is preoperatively dilated with topical G Phenylephrine 10% (Alcon Labs., Inc., China) and G Cyclopentolate 1% (Bausch & Lomb Pharm., Inc., USA) three times in one hour. The rabbits are anesthetized with ketamine hydrochloride (5 mg kg-1) and xylazine hydrochloride (2 mg kg-1) and placed on an operating table. A topical anesthetic (Dieaine hydrochloride 1%) is used every five minutes on two occasions. A wire lid speculum is placed to hold the eyelids open.

A 3.2 mm scleral tunnel incision into the eye is formed at the temporal limbus. The anterior chamber is maintained with viscoelastic substances and a 4-5 mm diameter continuous curvilinear capsularhexis (CCC) is made on the anterior surface of the lens to open its bag. The treatment solution is first introduced in the LECs by hydrodissection. This ensures that the treatment fluid immediately reaches under the entire anterior capsule/LECs. This process allows for (i) separation of the lens cortex from the capsule and lens epithelium, making removal of the lens cortex easier at a later stage of the operation and (ii) the LECs to be exposed to the treatment for enough time (more than five minutes in total time).

The crystalline lens is then removed using phacoemulsification (Universal II, Alcon Labs., Inc., China). The remaining cortex is aspirated thoroughly and removed as completely as possible to expose the LECs. The lens capsular bag is then partially filed with viscoelastic material in order to maintain its shape. The viscoelastic material should not cover the LECs when the treatment solution is applied.

The treatment is spread over the inner surface of the anterior capsular bag (where the LECs attach). The anterior capsular is continuously filled by using a syringe with a bent needle. Care is taken not to over flow the bag. After the treatment solution covered the capsule bag, it is left for five minutes and then removed using a syringe.

In a few cases, IOLs are inserted. In those cases, after the solution has covered the whole inner surface of the capsule bag, the treatment solution is carefully removed after 3 to 5 minutes by syringe. At the same time, the incision is enlarged to 6.0 mm and a posterior ocular lens (IOLs) (poly-methyl methacrylate, PMMA) with a 6.5 mm optic is prepared and placed into the capsular bag. Because this procedure normally takes a surgeon about five minutes, the LECs should have been exposed to the treatment solution for approximately ten minutes.

The capsular bag is then thoroughly rinsed with slight pressure to clear up the detached and dead LECs and remove excess treatment solution and viscoelastic material. The wound is closed with or without suture.

At the completion of the surgical procedure, each rabbit eye receives subconjunctival dexamethasone (0.25 ml) and gentamicin (0.25 ml). Postoperatively, atropine sulphate 1% ophthalmic solution and neomycin sulphate-polymyxin sulphate-dexamethasone ophthalmic ointment are administered twice daily for three weeks.

The animals are evaluated for three weeks and ten weeks. Three weeks is suggested in the literature to be optimal to demonstrate the preventative effect on PCO in rabbits. All rabbits are evaluated by slitlamp and scored for ocular responses at 1 day and at 1, 2 and 3 weeks. (See FIG. 17, Table 1.) Three and ten weeks after surgery, the animals are anesthetized using a 2 ml intramuscular injection of 11:1 mixture of ketamine hydrochloride and xylazine 20 mg/ml and then killed with a 2 ml intravenous injection of sodium pentobarbital.

The eye globes are enucleated (some of them fixed in neutral buffered formalin 10% solution for 24 hours) and are bisected coronally just anterior to the equator. Gross examination is performed to assess. PCO development. Photographs are taken from behind (Miyake-Apple posterior photographic technique) by using a digital camera fitted to an operating microscope (Leica/Wild MZ-8, Vashaw Scientific, Inc.).

The extent and severity of PCO is scored (see FIG. 17, Table 1) according to methods reported in the literature. The lens capsules are then fixed and evaluated under a microscope (Olumpus, Optical Co. Ltd.) and photographed with a digital camera. The absence or presence of cells, cell types, and the extent of cellular growth are determined.

The group treated with the treatment solution reveal minimal intraocular inflammatory reaction and deposits on the lens capsule surface at both 3 and 10 weeks post-treatment. No central PCO(CPCO) (the area within the pupillary area) and peripheral PCO (PPCO) (within 6-6.5 mm outside the pupillary area) is found to have developed three or ten weeks post-treatment. (See FIGS. 12C and 12D). Most eyes did develop some degree of Soemmering's ring associated with the amount of residual lens cortical fibers.

Figure 12:
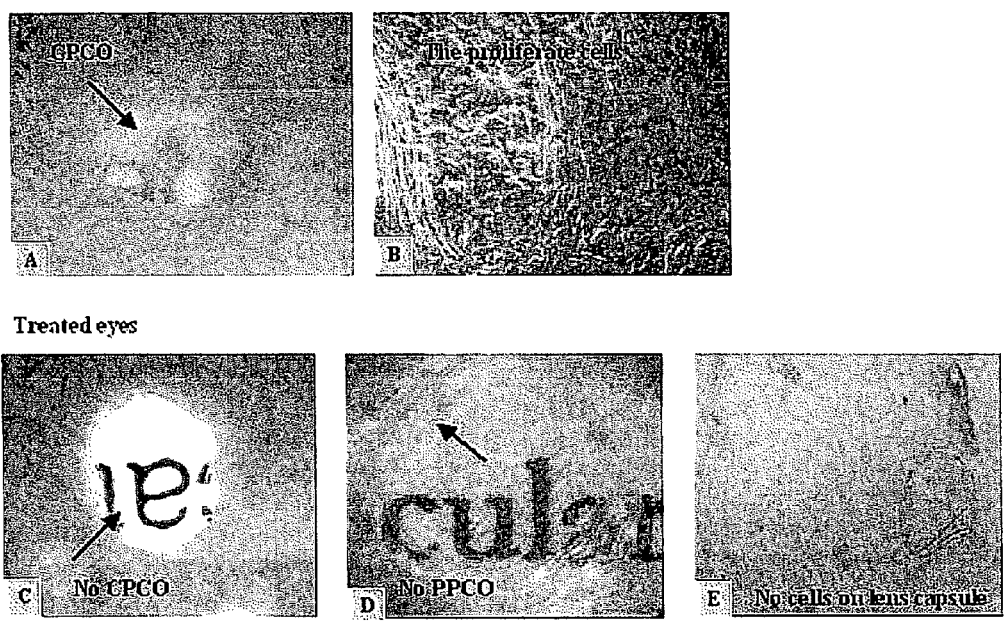
FIG. 12 is photographs illustrating the effects of treatment on in vivo rabbit eyes with a treatment solution containing DHCT and hyperosmotic NaCl in (C, D, E) treated eyes three weeks after surgery compared to (A, B) control eyes three weeks after surgery.

FIG. 12C is a gross photograph from behind the eye showing a treated rabbit eye after small incision cataract operation (no IOLs insertion) three weeks after surgery. The pupil area is clear. FIG. 12D is a gross photograph after removal of the iris. There is an absence of PPCO beyond the 6 mm central area. FIG. 12E is a phase contrast photomicrograph of the pupil area shown in FIG. 12C in which there appears to be no remaining lens epithelial cells.

In contrast to the treatment group, the eyes in the control group developed dramatic CPCO and PPCO. FIG. 12A is a gross photograph (taken from behind the eye using the Miyake-Apple technique) of a control rabbit eye 3 weeks after cataract operation (no IOLs insertion). There is significant fibrous from PCO in the pupil area. FIG. 12B, shows that under the microscope, there is significant proliferation of mixed pigmented and lens epithelial cells in the control eye, covering the entire lens capsule. (See FIG. 12B.)

Example 14

The in situ effects of a treatment solution comprising 308 μm bumetanide (a cotransport interference agent from the group of loop diuretics) and hyperosmotic 170 or 200 mM NaCl in $dH_2O$ on LECs-CCCs is examined. The LECs-CCCs are immediately used after being freshly removed from cataract operation and treatment is applied as in Example 12.

After exposure to the bumetanide-hyperosmotic NaCl treatment solution, the LECs shrink and gaps form between the cells. The shrunken cells do not round up but fix or arrest in the shrunken state on the lens capsule. The LECs do not detach, but arrest and die while shrunken. (See FIG. 13.)

Figure 13:
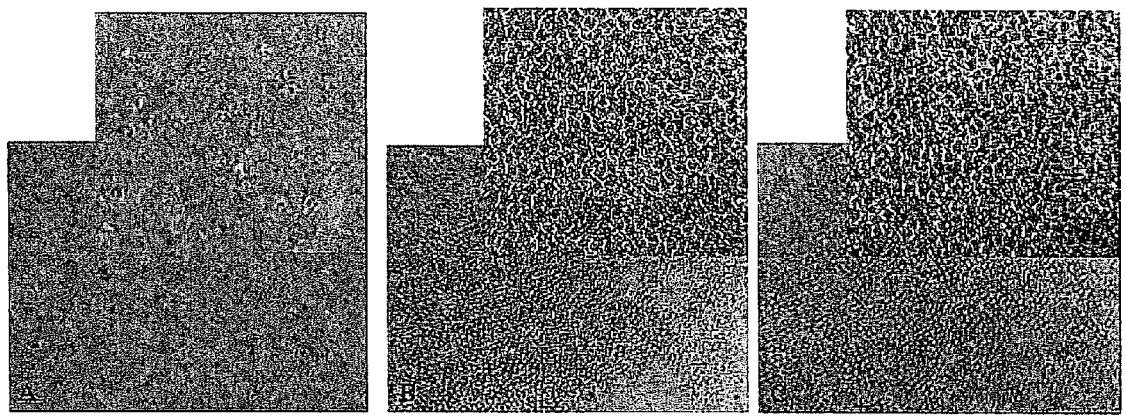
FIG. 13 is photographs illustrating the effects of treatment on LECs-CCCs with a treatment solution containing 308 μM bumetanide and hyperosmotic NaCl at (A) zero minutes, (B) five minutes and (C) after washing.

FIG. 13 shows the cellular changes of the LECs induced by treatment at (A) zero minutes, (B) five minutes and (C) after washing (fifteen minutes). FIG. 13A shows an intact lens epithelium sheet before the treatment with a few detached LECs, red blood cells and cell debris caused by the cataract operation. The inset is higher magnification of the image. FIG. 13B is taken five minutes post-treatment and shows cell shrinkage and large gaps between the cells. The inset is higher magnification of the image. FIG. 13C is taken fifteen minutes after washing away the treatment solution and any detached cells. The image shows the same appearance of shrinking cells as seen in FIG. 13B. The inset is higher magnification of the image. The cells died after treatment as confirmed by assessment by trypan blue exclusion.

Example 15

The in vivo efficacy of the treatment solution described in Example 14 (bumetanide and hyperosmotic NaCl) on the prevention of PCO is examined by experiments on two groups of New Zealand albino rabbits. The treatment group includes five rabbit eyes and the control group includes two eyes, established and assessed in parallel. The same surgical and evaluative procedures described in Example 13 are used in this experiment.

Figure 14:
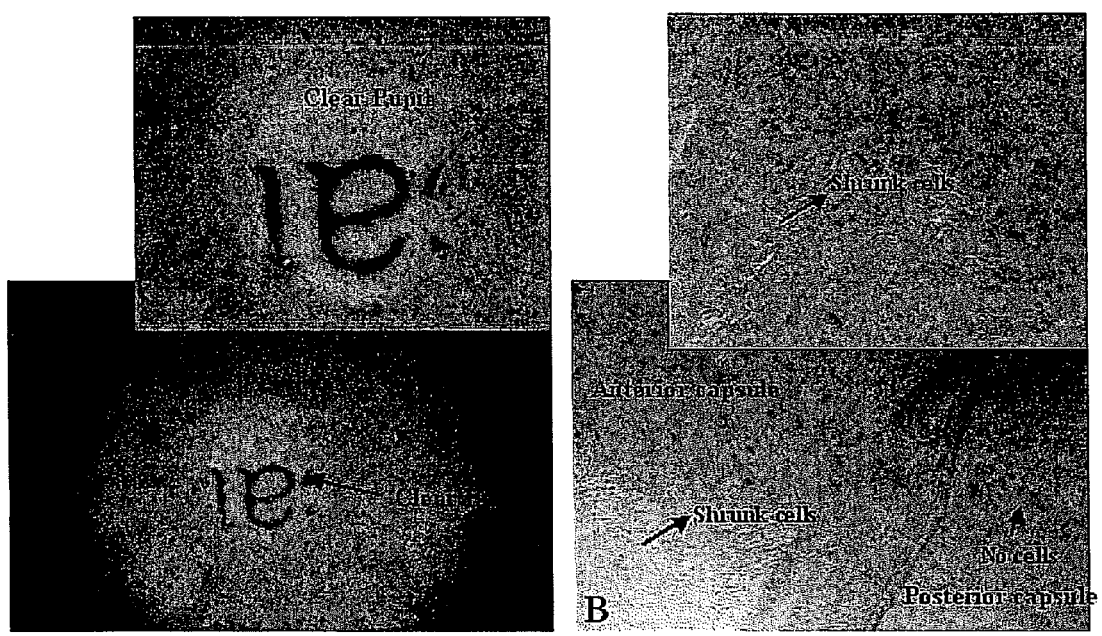
FIG. 14 is photographs illustrating the effects of treatment on in vivo rabbit eyes with a treatment solution containing bumetanide and hyperosmotic NaCl on treated rabbit eyes.

In three weeks follow up, the experiments reveal that no CPCO and PPCO develop in treated rabbits (observations made by gross examination from behind the eye using Miyake-Apple technique). (See FIG. 14.) Consistent with the results in situ (see Example 14), after exposure to the bumetanide-hyperosmotic NaCl solution, the whole monolayer of the lens epithelium is arrested in a shrunken appearance. This is only observed in the lens anterior capsule. (See FIG. 14B.) Not many cells in the lens posterior capsules are observed. Also, there is not significant cell proliferation on the lens anterior capsule although there is a monolayer of LECs with the described shrunken appearance.

FIG. 14A, a gross photograph taken from behind the eye using the Miyake-Apple technique, shows a clear pupil are in the treated rabbit eye three weeks after the cataract operation (no IOLs insertion). FIG. 14B, a phase-contrast photomicrograph taken from such pupils of the lens capsules after treatment, shows two layers of capsules. The top layer is the anterior capsule with a layer of shrunken cells. The bottom layer is the posterior capsule where there are no clear cells observed. The insets are higher magnifications of the images. The inset for FIG. 14B shows a monolayer of cells with a shrunken appearance and no significant proliferated cells.

Some degree of Soemmering's ring forms in the treated eyes, which appears associated with an ineffective cortical clean-up procedure.

In contrast to the results observed in the treatment eyes, there is significant fibrous growth from PCO observed in the pupil area of the control eyes, which are evaluated three weeks after cataract operation (no IOLs insertion).

Example 16

The in situ effects of a treatment solution comprising 200 or 300 μm N-ethylmaleimide (NEM) (a cotransport interference agent that activates or stimulates the efflux of KCl) in PBS on LECs-CCCs is examined. Treatment is applied as in Example 12.

After five minutes of acute exposure to the NEM treatment solution, almost no changes are observed in the LECs. However, once the treated LECs are put into a PBS washing solution, they shrink and large gaps form between the cells. The shrunken cells then detach from the LECs capsule as found in those described in Example 12.

Figure 15:
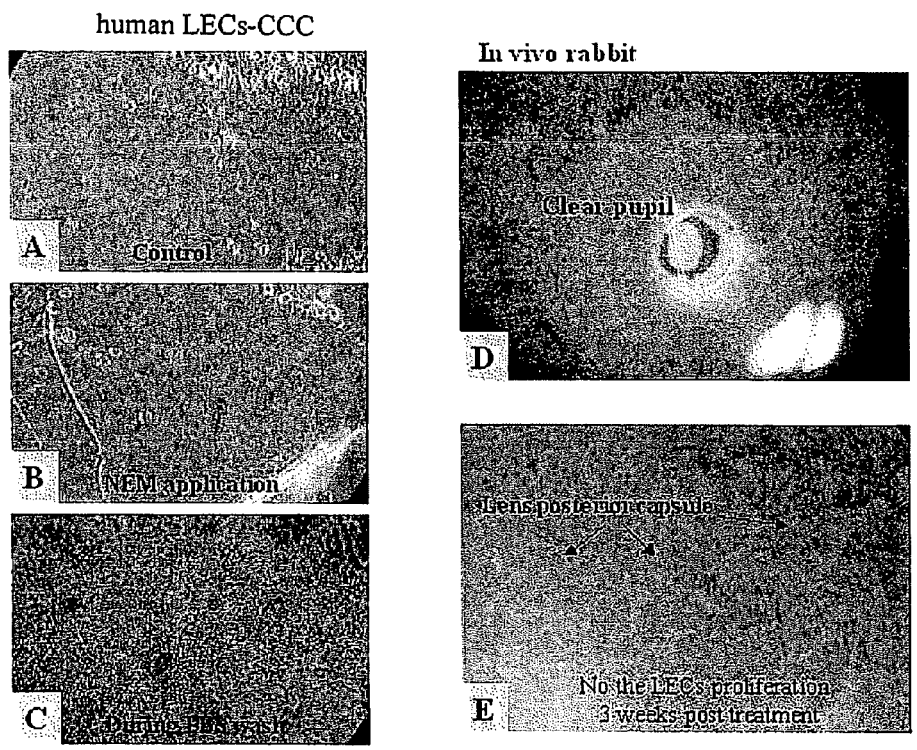
FIG. 15 is photographs illustrating the effects of treatment with a treatment solution containing NEM for human LECs at (A) zero minutes, (B) about three minutes and (C) two minutes after wash; and (D, E) on in vivo rabbit eyes.

FIG. 15 shows the cellular changes of the LECs-CCCs induced by the NEM treatment at (A) zero minutes, (B) two to three minutes and (C) two minutes after wash. FIG. 15A shows an intact lens epithelium sheet before treatment with some damages and detached LECs and cellular debris caused by the cataract operation. FIG. 15B, taken two to three minutes post-treatment, shows slight cell shrinkage. Once the cells are placed back in fresh PBS washing solution, the cells shrink significantly and large gaps form between the cells. These cells then detach and wash away easily at the end of the experiments.

Example 17

The in vivo efficacy of the treatment solution generally described in Example 16 (NEM in PBS) on the prevention of PCO is examined by experiments on two groups of New Zealand albino rabbits. The treatment group includes six rabbit eyes and the control group includes two rabbit eyes, established and assessed in parallel. The surgical and evaluative procedures in Example 13 are used.

The eyes in the treatment group are treated with 200 or 300 μm NEM in PBS or 170 mM monnitol. In 3 and 10 weeks follow up, no CPCO or PPCO develops in the treated rabbits (observed in gross examination from behind the eyes). (See FIG. 17, Table 1 and FIG. 15D.) The pupil area of treated eyes is clear. There are no LECs on the lens capsule bag when it is examined under microscope. (FIG. 15E.) However, the treated eyes exhibit a heavy intraocular inflammatory reaction in the early period and posterior synechiae.

In contrast to the results observed in the treatment eyes, there is significant fibrous growth from PCO observed in the pupil area of the two control rabbit eyes (no IOLs insertion).

Example 18

The procedure by which treatment is applied to in vivo eyes is modified to prevent heavy anterior chamber (AC) reaction. Instead of introducing the treatment solution directly into the eyes, the IOLs are coated with treatment solution and are inserted into the lens capsular bag after the lens contents are removed. Specifically, the posterior and equator portion of the IOLs are coated with the treatment solution containing 300 μm NEM in PBS. They are then dried overnight in a sterile Laminar flow hood. The IOLs are then ready to use. This procedure significantly reduces the AC reaction.

Example 19

The in situ effects of a treatment solution comprising 10 or 100 μm gramicidin (an agent from the class of pore-forming proteins and peptides (PFPs)) and PBS on human LECs is examined. Treatment is applied as in Example 12.

Figure 16:
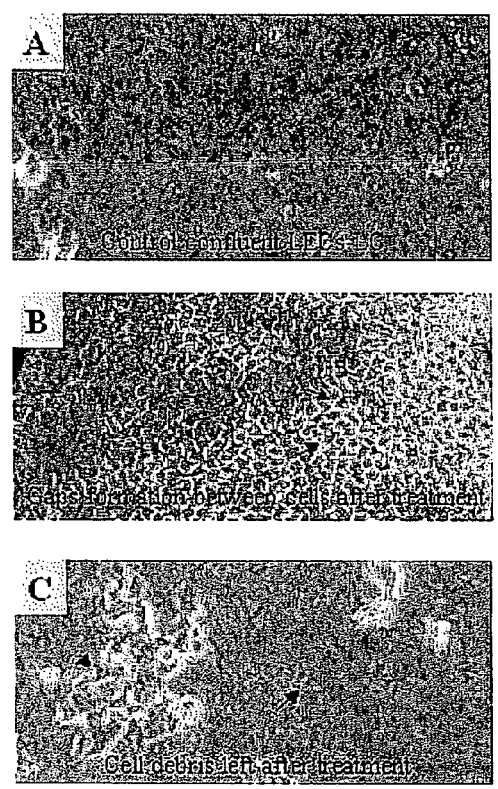
FIG. 16 is photographs illustrating the effects of treatment on LECs-CCCs with a treatment solution containing gramicidin and PBS at (A) zero minutes (B) two minutes and (C) after wash.

The LECs-CCCs are exposed to the gramicidin-PBS treatment solution for five minutes. Changes to the LECs are monitored under microscope. FIG. 16 shows microscope photographs taken at (A) zero minutes (B) two minutes and (C) after wash.

After exposure to the treatment, the human LECs shrink and large gaps gradually form between the cells. The shrinking cells then gradually round up and burst. FIG. 16A, taken before treatment solution is applied, shows lens cells in tight contact with each other and resembling an intact sheet of cells. FIG. 16B shows that, at two minutes after exposure to the treatment solution, the cells take on a shrunken appearance and clear gaps between the cells form. FIG. 16C shows that, after the treatment solution and detached cells have been rinsed away, no living cells remain apart from some remaining cell debris.

Many modifications and variations of the present invention are possible in light of the above teachings. For example, other ion transport mechanism interference agents may be used than those discussed above in detail such as the following which may be appropriate: valinomycin, bromine, theophylline and other alkylxanthines, icosanoids, phorbol ester (e.g. TPA), potassium-sparing diuretics (e.g., triamterene, spironolactone, and potassium canrenoate), calyculin A, okadaic Acid (OA), propranolol and its analogs, Angiotensin II, Ketoconazole (CDC), arachidonic acid, ianthanum, trifluoperazine, idoxifene, 2-aminisobutyric acid, 17 beta-oestradiol, Bradykinin, phosphatidylinositol 4,5-biphosphate (PIP2), inositol 1,4,5, triphosphate (IP3), prostaglandins ($PGE_2$), adenosine 3'5'-cyclic monophosphate (cAMP), guanosine 3'5'-cyclic monophosphate (cGMP), serine/threonine protein phosphatases (S/T-Ppases), protein kinase C (PKC), protein kinase A (PKA), mitogen-activated protein kinase (MAPK), SRC family tyrosine kinases (SFKs), polyunsaturated fatty acids, phospholipase C (PLC), phosphatases (PP), G-proteins, Rubidium, Copper ($Cu^{2+}$), Nitrate ($NO^{3-}$), Barium ($Ba^{2+}$), Chloride ($Cl^-$), Potassium ($K^+$), agents that change intracellular magnesium and hydrogen concentration, and agents that decrease extracellular sodium, chloride or potassium concentrations. It should be appreciated that there are other ion transport mechanism interference agents as well. Thus, it is to be understood that, within the scope of the appended claims, the invention may be practiced otherwise than as described hereinabove.

What is claimed and desired to be secured by Letters Patent is:

1. An ocular treatment solution, having a pH of about 7 to 10, comprising:
   an ion transport mechanism interference agent and an osmolyte wherein the solution induces substantially greater incidence of detachment of lens epithelial cells than corneal endothelial cells and retinal pigmented epithelial cells to prevent posterior capsular opacification and wherein the lens epithelial cells shrink prior to detachment.

2. An ocular treatment solution as recited in claim 1 wherein the ion transport meeltanisrn interference agent is a co-transport interference agent.

3. An ocular treatment solution as recited in claim 2 wherein the co-transport interference agent is selected from the group of diuretics.

4. An ocular treatment solution as recited in claim 3 wherein the co-transport interference agent is dihydrochlorothiazide.

5. An ocular treatment solution as recited in claim 4 wherein the osmolyte comprises an inorganic salt.

6. An ocular treatment solution as recited in claim 5 wherein the treatment solution has a hyperosmotic osmolarity and wherein dihydrocltlorothiazdc is present in the solution in a concentration ranging from about 60 μM to about 500 μM.

7. An ocular treatment solution as recited in claim 3 wherein the co-transport interference agent is bumetanide.

8. An ocular treatment solution as recited in claim 1 wherein the osmolyte comprises an inorganic salt.

9. An ocular treatment solution as recited in claim 8 wherein the treatment solution has a hyperosmotic osmolarity and wherein bumetanide is present in the solution in a concentration ranging from about 30 μM to about 500 μM.

10. An ocular treatment solution as recited in claim 2 wherein the co-transport interference agent is n-ethylmaleimide.

11. An ocular treatment solution as recited in claim 10 wherein n-ethylmaleimide is present in the solution in a concentration ranging from about 100 µM to about 500 µM.

12. An ocular treatment solution as recited in claim 1 wherein the ion transport mechanism interference agent comprises a pore-forming protein or peptide.

13. An ocular treatment solution as recited in claim 12 wherein the pore-forming protein or peptide is gramicidin.

14. An ocular treatment solution as recited in claim 13 wherein gramicidin is present in the solution in a concentration ranging from about 10 µM to about 300 µM.

15. An ocular treatment solution comprising: an ion transport mechanism interference agent and an osmotic stress agent to prevent posterior capsular opacitication, the solution having a pH from about 7 to about 10 and the solution rapidly inducing death via necrosis of lens epithelial cells.

16. An ocular treatment solution as recited in claim 1 wherein the ion transport interference agent is present in the solution in a concentration less than about 1500 µM.

17. An ocular treatment solution as recited in claim 1 wherein the ion transport interference agent is present in the solution in a concentration less than about 1000 µM.

18. An ocular treatment solution as recited in claim 1 wherein the ion transport interference agent is present in the solution in a concentration less than about 500 µM.

19. An ocular treatment solution as recited in claim 3 wherein the diuretic is a thiazide diuretic.

* * * * *